(12) United States Patent
Srivastava et al.

(10) Patent No.: US 11,208,389 B2
(45) Date of Patent: Dec. 28, 2021

(54) COMPOSITIONS AND METHODS FOR REDUCING CELL VIABILITY

(71) Applicant: GLAX LLC, Wilmington, DE (US)

(72) Inventors: Rakesh K Srivastava, New Orleans, LA (US); Sharmila Shankar, New Orleans, LA (US); Sushant Kumar Shrivastava, Benares (IN); Anupam G. Banerjee, Benares (IN)

(73) Assignee: GLAX LLC, Wilmington, DE (US)

( * ) Notice: Subject to any disclaimer, the term of this patent is extended or adjusted under 35 U.S.C. 154(b) by 0 days.

(21) Appl. No.: 16/397,345

(22) Filed: Apr. 29, 2019

(65) Prior Publication Data

US 2019/0330165 A1 Oct. 31, 2019

Related U.S. Application Data

(60) Provisional application No. 62/664,836, filed on Apr. 30, 2018.

(51) Int. Cl.
| | | |
|---|---|---|
| *C07D 253/07* | (2006.01) | |
| *C07D 253/06* | (2006.01) | |
| *A61K 31/53* | (2006.01) | |
| *C07D 403/06* | (2006.01) | |
| *C07D 417/06* | (2006.01) | |
| *C07D 413/06* | (2006.01) | |
| *A61K 45/06* | (2006.01) | |

(52) U.S. Cl.
CPC ............ *C07D 253/07* (2013.01); *A61K 31/53* (2013.01); *A61K 45/06* (2013.01); *C07D 253/06* (2013.01); *C07D 403/06* (2013.01); *C07D 413/06* (2013.01); *C07D 417/06* (2013.01)

(58) Field of Classification Search
CPC .. C07D 403/06; C07D 417/06; C07D 413/06; C07D 253/06; C07D 253/07; A61K 45/06
USPC ........................................................ 514/242
See application file for complete search history.

(56) References Cited

PUBLICATIONS

Simultaneous quantitation of Hoechst 33342 and immunofluorescence on viable cells using a fluorescence activated cell sorter; LOKEN, Cytometry, 1980; 1:136.*
Banijamali et al., Journal of Heterocyclic Chemistry (1986), 23(6), 1613-16 .*
El-Sayed et al., Synthesis and antitumor activity of new 1,2,4-triazine and [1,2,4]triazolo[4,3-b]triazine derivatives and their thioglycoside and acyclic C-nucleoside analogs.*

* cited by examiner

*Primary Examiner* — Tracy Vivlemore
*Assistant Examiner* — Ebenezer O Sackey

(57) ABSTRACT

This invention is directed to compositions, methods and kits that can be used for reducing cell viability, inducing cell apoptosis, and inhibiting cell proliferation, such as for the treatment of cancer. The invention is also directed to compositions, methods and kits that can be used for treating inflammatory conditions, such as by modulating inflammatory cytokines.

45 Claims, 19 Drawing Sheets

(S₂4a-S₂4e)

| S. No. | Compound | Ar |
|---|---|---|
| 1 | S₂2a | Phenyl |
| 2 | S₂2b | 4-Methylphenyl |
| 3 | S₂2c | 4-Methoxyphenyl |
| 4 | S₂2d | 4-Chlorophenyl |
| 5 | S₂2e | 4-Nitrophenyl |
| 6 | S₂3a | Phenyl |
| 7 | S₂3b | 4-Methylphenyl |
| 8 | S₂3c | 4-Methoxyphenyl |
| 9 | S₂3d | 4-Chlorophenyl |
| 10 | S₂3e | 4-Nitrophenyl |
| 11 | S₂4a | Phenyl |
| 12 | S₂4b | 4-Methylphenyl |
| 13 | S₂4c | 4-Methoxyphenyl |
| 14 | S₂4d | 4-Chlorophenyl |
| 15 | S₂4e | 4-Nitrophenyl |

| S.No | Ligand | Protein | Docking Score | Glide Score (Kcal/Mole) | Interacting Residues | Bond Type |
|---|---|---|---|---|---|---|
| 1 | SST-13 | COX-1 | -7.82 | -7.864 | SER-530,ARG-120,ARG-513,HIS-90 | Hydrophobic Interaction |
| | | COX-2 | -7.441 | -7.486 | VAL-523,PHE-518,ARG-513,HIS-90 | Hydrophobic Interaction |
| | | 5-LOX | -5.044 | -5.089 | HIS-367,HIS-372, PHE-177,LEU-607, | 1 Hydrogen bonding, Other hydrophobic interaction |

*FIG. 15*

COMPOSITIONS AND METHODS FOR REDUCING CELL VIABILITY

This application claims priority from U.S. Provisional Application No. 62/664,836 filed on Apr. 30, 2018.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to compositions, methods and kits that can be used for reducing cell viability, inducing cell apoptosis, and inhibiting cell proliferation, such as for the treatment of cancer. The invention is also directed to compositions, methods and kits that can be used for treating inflammatory conditions, such as by modulating inflammatory cytokines.

BACKGROUND OF THE INVENTION

Cyclooxygenase (COX) is the key enzyme of arachidonic acid metabolism. Arachidonic acid metabolite, generated by COX, is implicated in cancer pathogenesis, for example the colorectal cancer (CRC) pathogenesis. The development of anti-cancer drugs targeting COX-2 has been limited by unwanted toxic side effects.

SUMMARY OF THE INVENTION

The invention provides for compounds for treating cancer.

Aspects of the invention are directed towards a compound of Formula I:

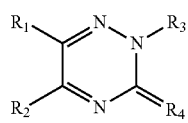
(I)

wherein, $R_1$ is an aryl; $R_2$ is an aryl; $R_3$ is H; and $R_4$ is O or S.

In an embodiment, the aryl is phenyl.
In an embodiment, the compound is:

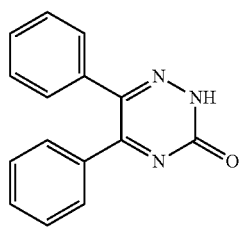 [SMILES: O=c1nc(-c2ccccc2)c(-c2ccccc2)n[nH]1]

In an embodiment, the compound is:

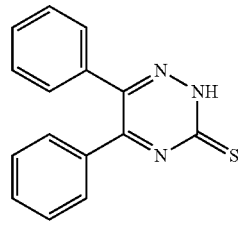 [SMILES: S=c1nc(-c2ccccc2)c(-c2ccccc2)n[nH]1]

Aspects of the invention are directed towards a compound of Formula II:

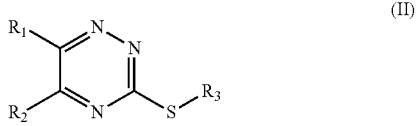
(II)

wherein $R_1$ is an aryl; $R_2$ is an aryl; and $R_3$ is —$CH_2$—CO—$OC_2H_5$ or —$C_2H_5$.

In an embodiment, the aryl is phenyl.
In an embodiment, the compound is:

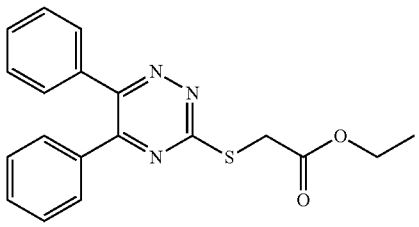

In an embodiment, the compound is:

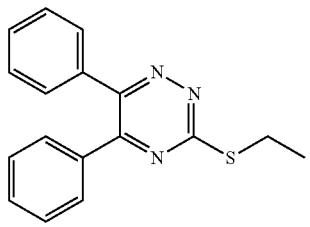

Aspects of the invention are further directed towards methods of reducing cell viability comprising contacting a cell with an effective amount of a compound described herein.

Aspects of the invention are still further directed towards methods of inducing apoptosis of a cell comprising contacting a cell with an effective amount of a compound described herein.

Aspects of the invention are also directed towards methods of inhibiting cell proliferation comprising contacting a cell with an effective amount of a compound described herein.

Still further, aspects of the invention are directed towards methods of regulating epithelial-mesenchymal transition (EMT) comprising contacting a cell with an effective amount of a compound described herein.

Yet further, aspects of the invention are directed towards methods of inhibiting tumor growth comprising contacting a cell with an effective amount of a compound described herein.

In embodiments, the compound comprises

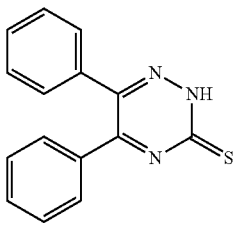

and/or

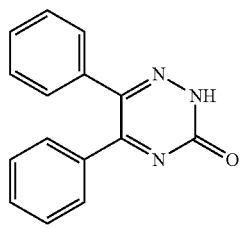

In embodiments, the compound comprises

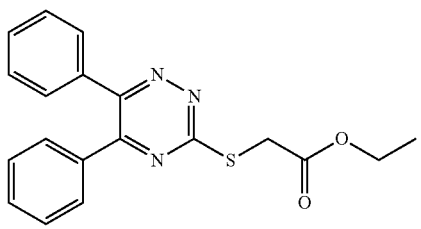 [SMILES: CCOC(=O)CSc1nnc(-c2ccccc2)c(-c2ccccc2)n1]

and/or

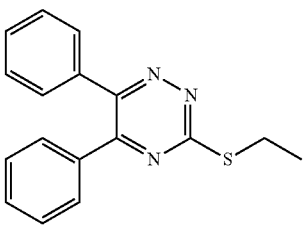 [SMILES: CCSc1nnc(-c2ccccc2)c(-c2ccccc2)n1]

Embodiments comprise a pharmaceutical composition comprising a compound described herein and a pharmaceutically acceptable carrier.

Embodiments can further comprise a second active agent, for example a non-steroidal anti-inflammatory drug (NSAID), a selective COX-2 inhibitor, a non-selective COX inhibitor, or a combination thereof. Non-limiting examples of the selective COX-2 inhibitor comprises celecoxib, refecoxib, parecoxib and valdecoxib.

Aspects of the invention are directed towards methods of reducing cell viability comprising contacting a cell with an effective amount of a compound of Formula IV

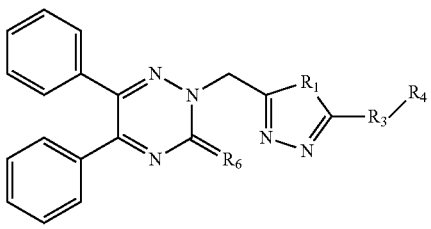

wherein, $R_1$ is O, S, or $N(R_2)$; $R_2$ is an aryl group; $R_3$ is $N(R_5)$, or S; $R_4$ is H; $R_5$ is an aryl group; and $R_6$ is O or S.

Aspects of the invention are directed towards methods of inducing apoptosis of a cell comprising contacting a cell with an effective amount of a compound of Formula IV:

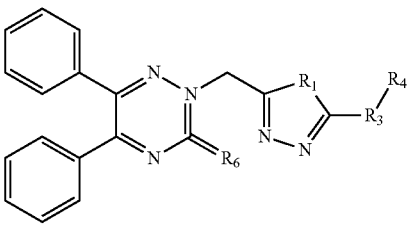

wherein, $R_1$ is O, S, or $N(R_2)$; $R_2$ is an aryl group; $R_3$ is $N(R_5)$, or S; $R_4$ is H; $R_5$ is an aryl group; and $R_6$ is O or S.

In embodiments, apoptosis comprises caspase-dependent apoptosis, such as caspase 3 dependent apoptosis and/or caspase 7 dependent apoptosis.

In embodiments, the compound modulates levels of survivin, Bcl-2, and Bax.

Aspects of the invention are directed towards methods of inhibiting cell proliferation comprising contacting a cell with an effective amount of a compound of Formula IV:

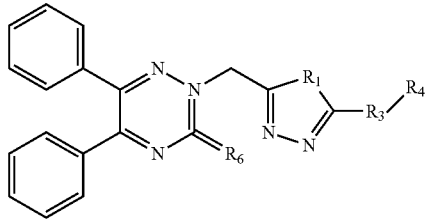

wherein, $R_1$ is O, S, or $N(R_2)$; $R_2$ is an aryl group; $R_3$ is $N(R_5)$, or S; $R_4$ is H; $R_5$ is an aryl group; and $R_6$ is O or S.

In embodiments, cell proliferation is indicated by measuring TCF/LEF1 activity.

Aspects of the invention are directed towards methods of regulating epithelial-mesenchymal transition (EMT) comprising contacting a cell with an effective amount of a compound of Formula IV:

(IV)

[Chemical structure of Formula IV showing diphenyl triazine connected to a five-membered heterocycle with R1, R3, R4, R6 substituents]

wherein, $R_1$ is O, S, or $N(R_2)$; $R_2$ is an aryl group; $R_3$ is $N(R_5)$, or S; $R_4$ is H; $R_5$ is an aryl group; and $R_6$ is O or S.

Aspects of the invention are directed towards methods of inhibiting tumor growth comprising contacting a cell with an effective amount of a compound of Formula IV:

(IV)

[Chemical structure of Formula IV]

wherein, $R_1$ is O, S, or $N(R_2)$; $R_2$ is an aryl group; $R_3$ is $N(R_5)$, or S; $R_4$ is H; $R_5$ is an aryl group; and $R_6$ is O or S.

In embodiments, tumor growth is inhibited by inducing cellular apoptosis and/or inhibiting cellular proliferation.

In embodiments, the aryl group is phenyl.

In embodiments, the compound comprises the following chemical structure:

[Chemical structure with oxadiazole-NHAr group]

In embodiments, the compound comprises the following chemical structure:

[Chemical structure with thiadiazole-NHAr group]

In embodiments, the compound comprises the following chemical structure:

[Chemical structure with triazole-SH group and Ar substituent]

In embodiments, the cell comprises a cancer cell, such as a colorectal/colon cancer cell, pancreatic cancer cell, or lung cancer cell.

Aspects of the invention are directed towards methods of suppressing an inflammatory response comprising contacting a cell with an effective amount of a compound described herein.

Aspects of the invention are directed towards methods of modulating an inflammatory cytokine in a cell comprising contacting a cell with an effective amount of a compound described herein. For example, the cytokine comprises a pro-inflammatory cytokine (IL-6, IL-8, TNFα, IL-1β), an anti-inflammatory cytokine (IL4), and/or a chemokine (CCL2).

In embodiments, the compound is administered to a subject prior to contacting.

In embodiments, the compound is administered in a single dose.

In embodiments, the compound is administered continuously.

In embodiments, the compound is administered at intervals of about 4 hours, 12 hours, or 24 hours.

In embodiments, the compound is administered orally, parentally, transdermally, or nasally.

In embodiments, the compound exhibits anti-cancer effect while the risk of toxicity is reduced.

In embodiments, the compound exhibits anti-inflammatory effect while the risk of toxicity is reduced Non-limiting examples of toxicity comprises cardiotoxicity, gastrotoxicity, hepatotoxicity, nephrotoxicity, or a combination thereof.

Embodiments can further comprise measuring serum biomarkers indicative of cardiac function, stomach function, liver function, kidney function, or a combination thereof. Non-limiting examples of biomarkers indicative of cardiac function comprise serum cardiac troponin-I (cTnI), serum creatine kinase-MB (CK-MB), or a combination thereof. Non-limiting examples of biomarkers indicative of liver function and/or kidney function comprise serum enzymes, total protein, and total albumin.

Aspects of the invention are also directed towards a medical kit suitable for the treatment of cancer, comprising printed instructions for administering a compound described herein to a subject afflicted with a cancer; or a pharmaceutical composition comprising a compound described herein and a pharmaceutically acceptable carrier. In embodiments, the compound is a selective, COX-2 inhibitor.

Aspects of the invention are also directed towards methods of treating a neurological disorder comprising administering to a subject afflicted with a neurological disorder a therapeutically effective amount of a compound described herein.

Other objects and advantages of this invention will become readily apparent from the ensuing description.

BRIEF DESCRIPTION OF THE FIGURES

FIG. 15 shows SST-13 docking analysis.

DETAILED DESCRIPTION OF THE INVENTION

Abbreviations and Definitions

Figure 1:
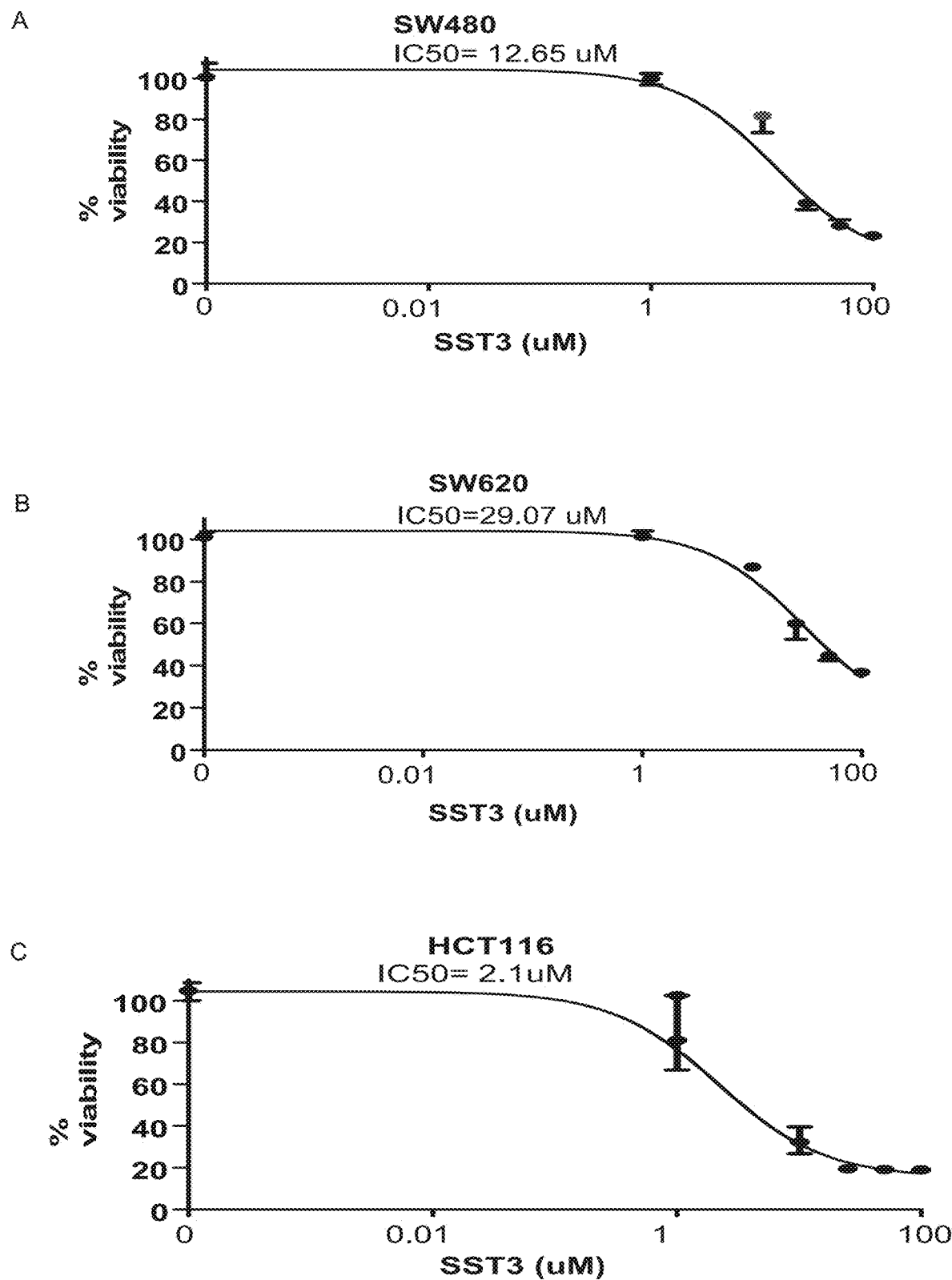
FIG. 1 shows SST3 inhibits cell viability in colorectal cancer. (A-C), CRC cell lines were seeded in 96-well plate, treated with SST3 for 72 hrs and XTT assay was performed. Data represent mean±SD (n=4).
Figure 2:
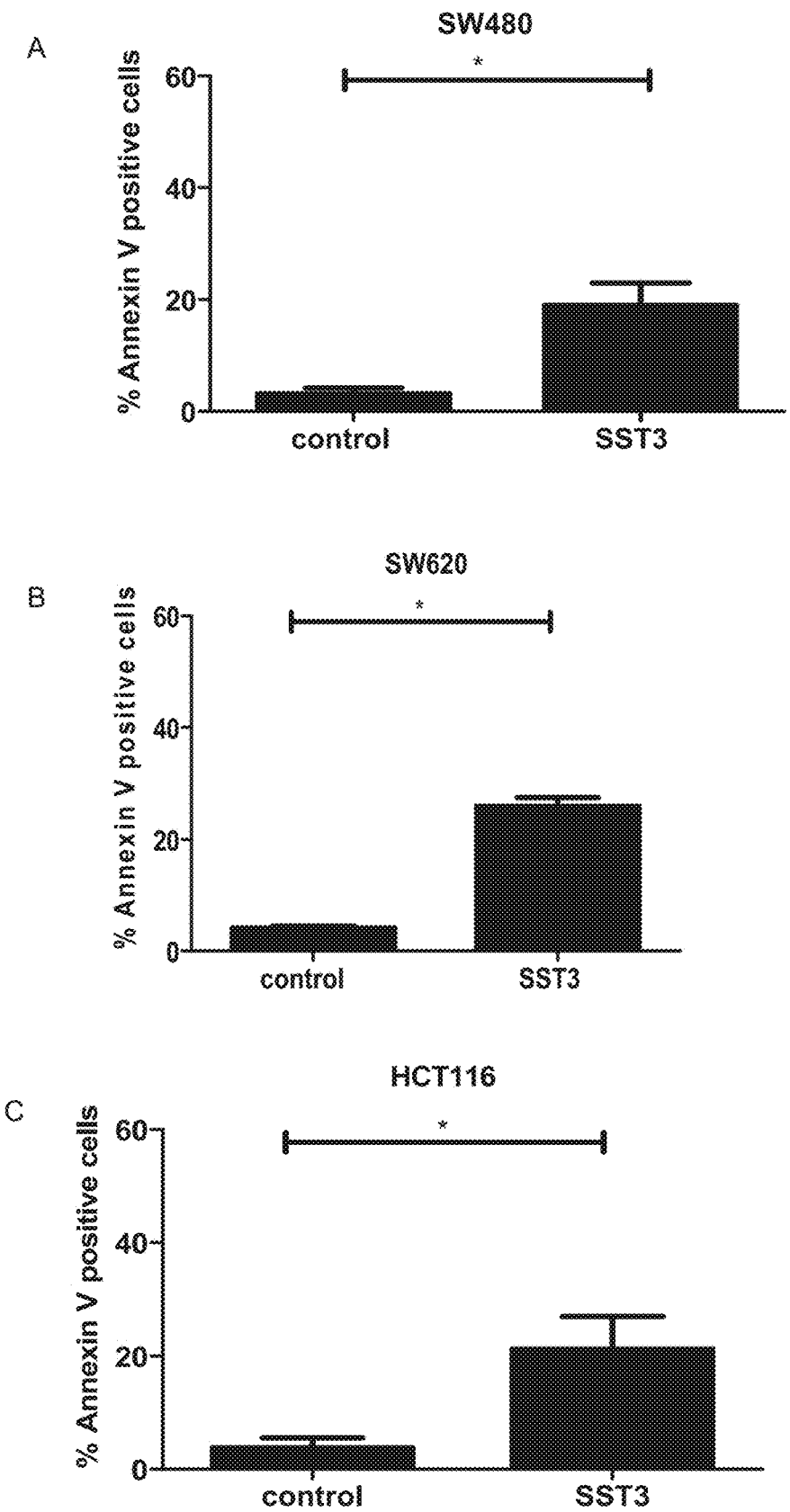
FIG. 2 shows SST3 induces apoptosis in colorectal cancer. (A-C), Apoptosis assay. Cells were treated with SST3 (5 μM) for 72 hrs. At the end of incubation period, cells were harvested and annexin-V/PI staining was performed. Data represent mean±SD (n=4).
Figure 3:
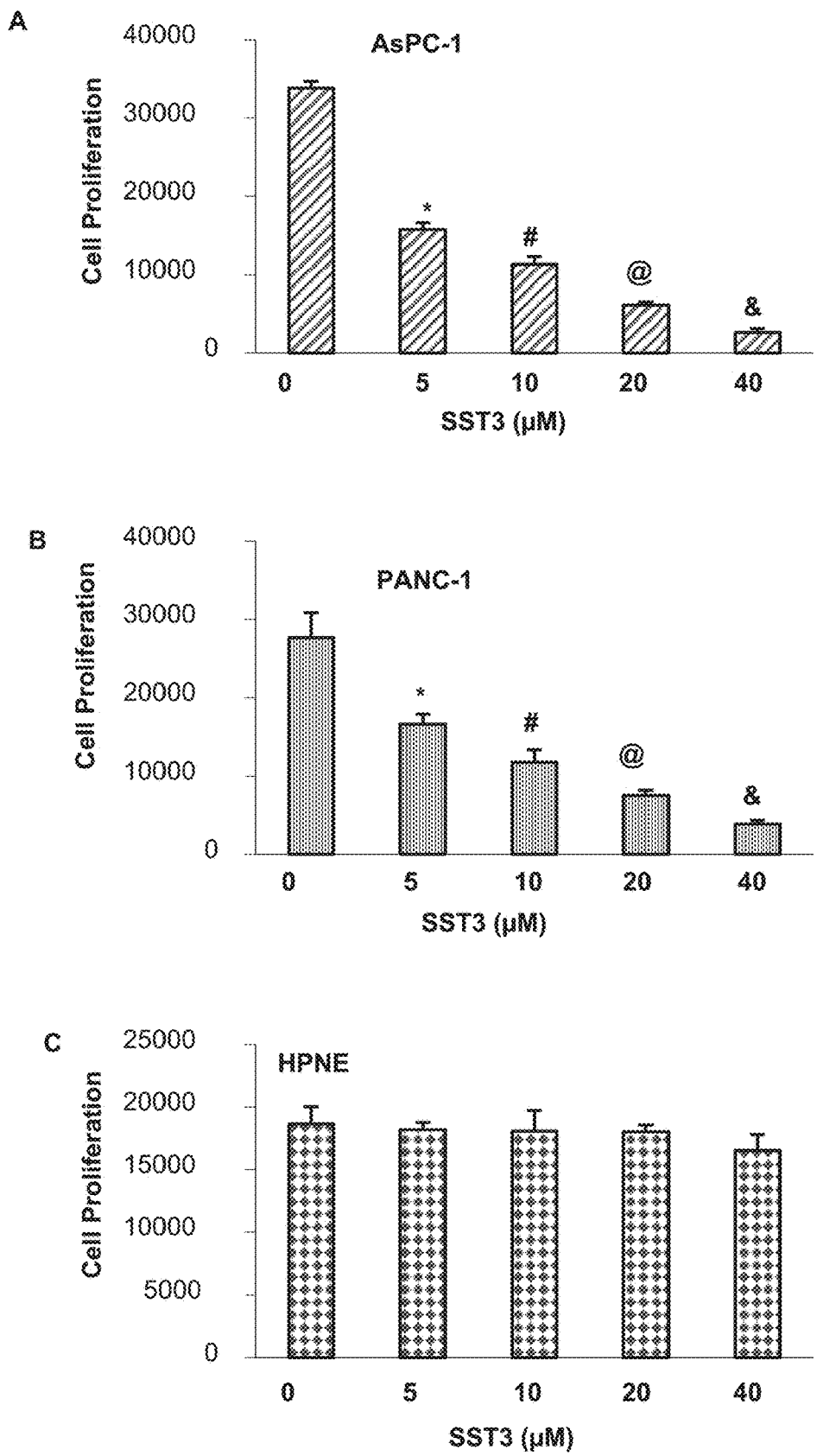
FIG. 3 shows SST3 inhibits cell proliferation of pancreatic cancer cells. (A-B), Pancreatic cancer AsPC-1 and PANC-1 cells were treated with SST3 (0-40 uM) for 72 hrs. At the end of incubation period, viable cells were counted by trypan blue assay. Data represent mean±SD (n=4). (C), Human pancreatic normal ductal epithelial (HPNE) cells were treated with SST3 (0-40 uM) for 72 hrs. At the end of incubation period, viable cells were counted by trypan blue assay. Data represent mean±SD (n=4).
Figure 4:
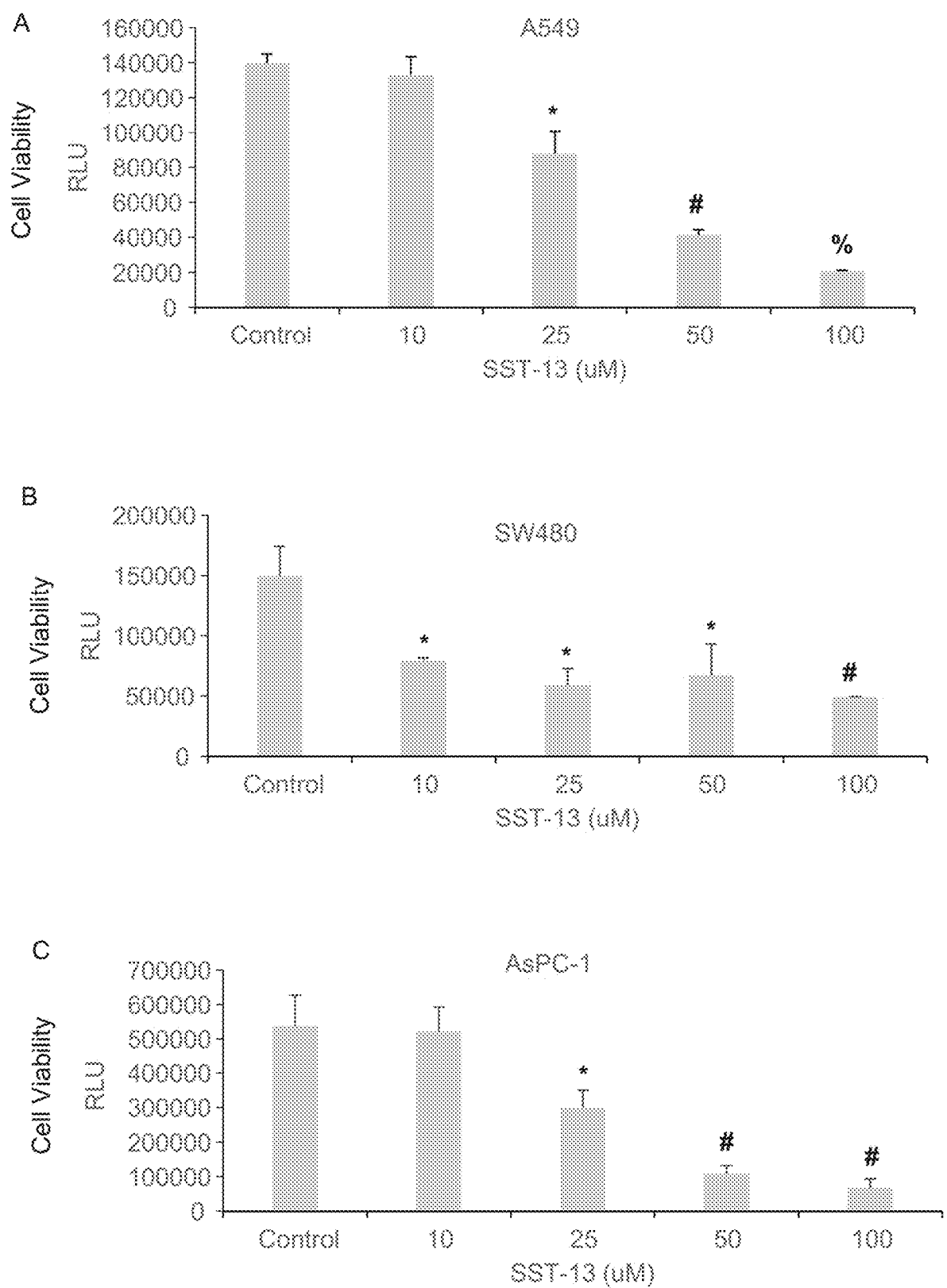
FIG. 4 shows SST13 inhibits cell viability in various cancer cells. Human lung (A549), colon (SW480) and pancreatic (AsPC-1) cancer cells were treated with SST13 (0-100 uM) for 72 hrs. At the end of incubation period, cell viability was measured by CellTiter-Glo® Luminescent Cell Viability Assay (Promega). Data represent mean±SD (n=4).
Figure 5:
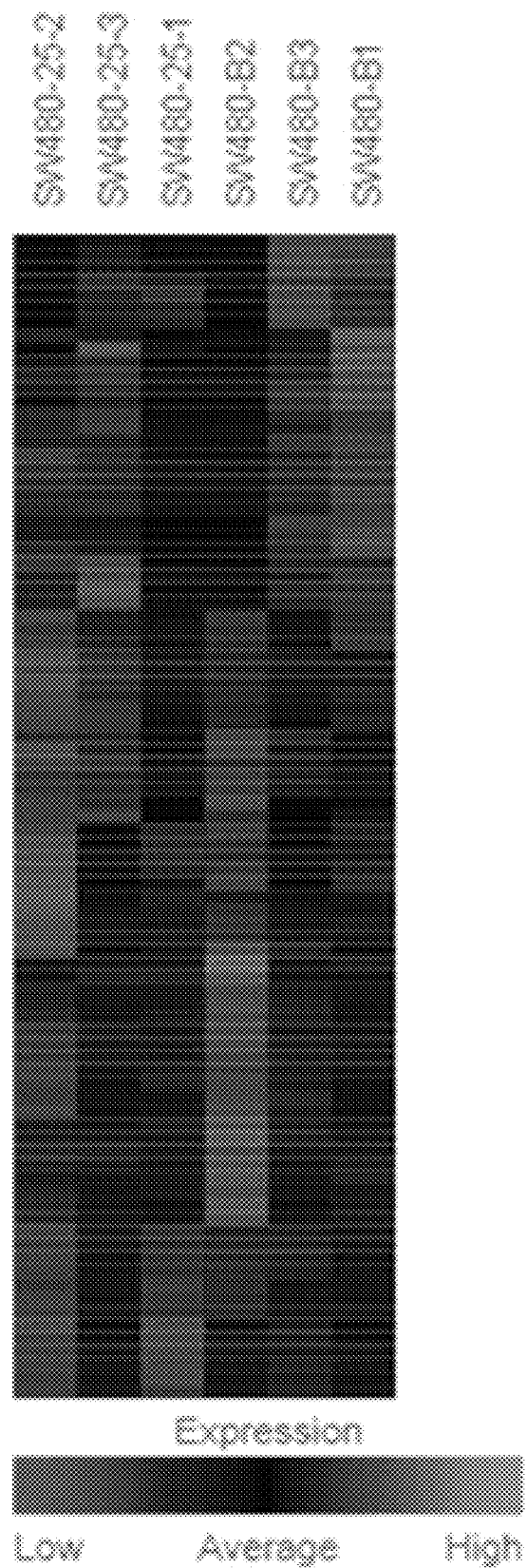
FIG. 5 shows gene signature of SST3 in colorectal cancer. SW-480 cells were treated with SST3 for 36 hrs. RNA was isolated (n=3) and subjected to RNA sequencing (HiSeq 3000) as per manufacture's instruction (Illumina).
Figure 6:
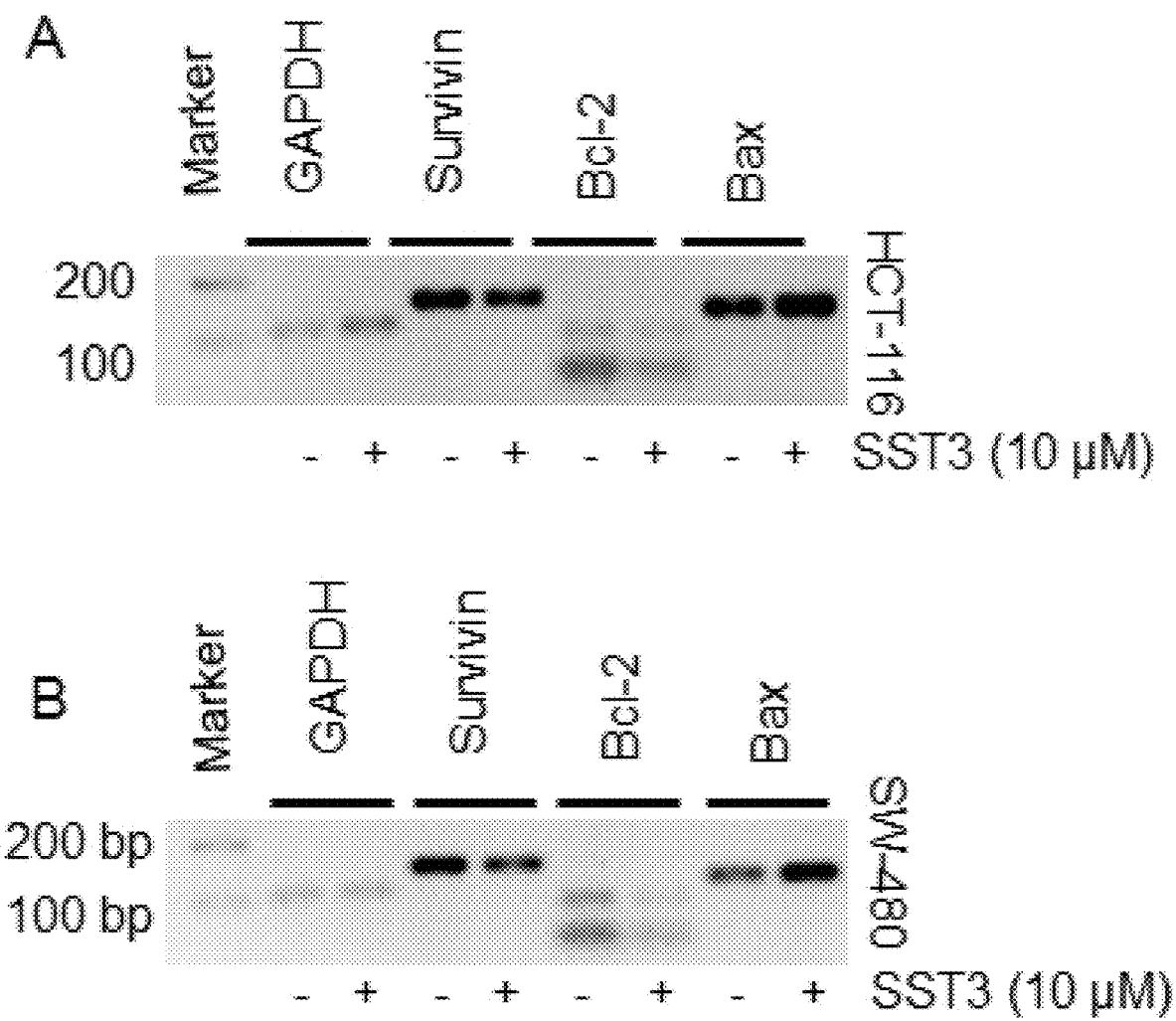
FIG. 6 shows regulation of survivin, Bcl-2 and Bax by SST3 in colorectal cancer. Colorectal cancer (HCT-116 and SW-480) cells were treated with SST3 (10 μM) for 36 hrs. The expression of Survivin, Bcl-2 and Bax genes was measured by RT-PCR.
Figure 7:
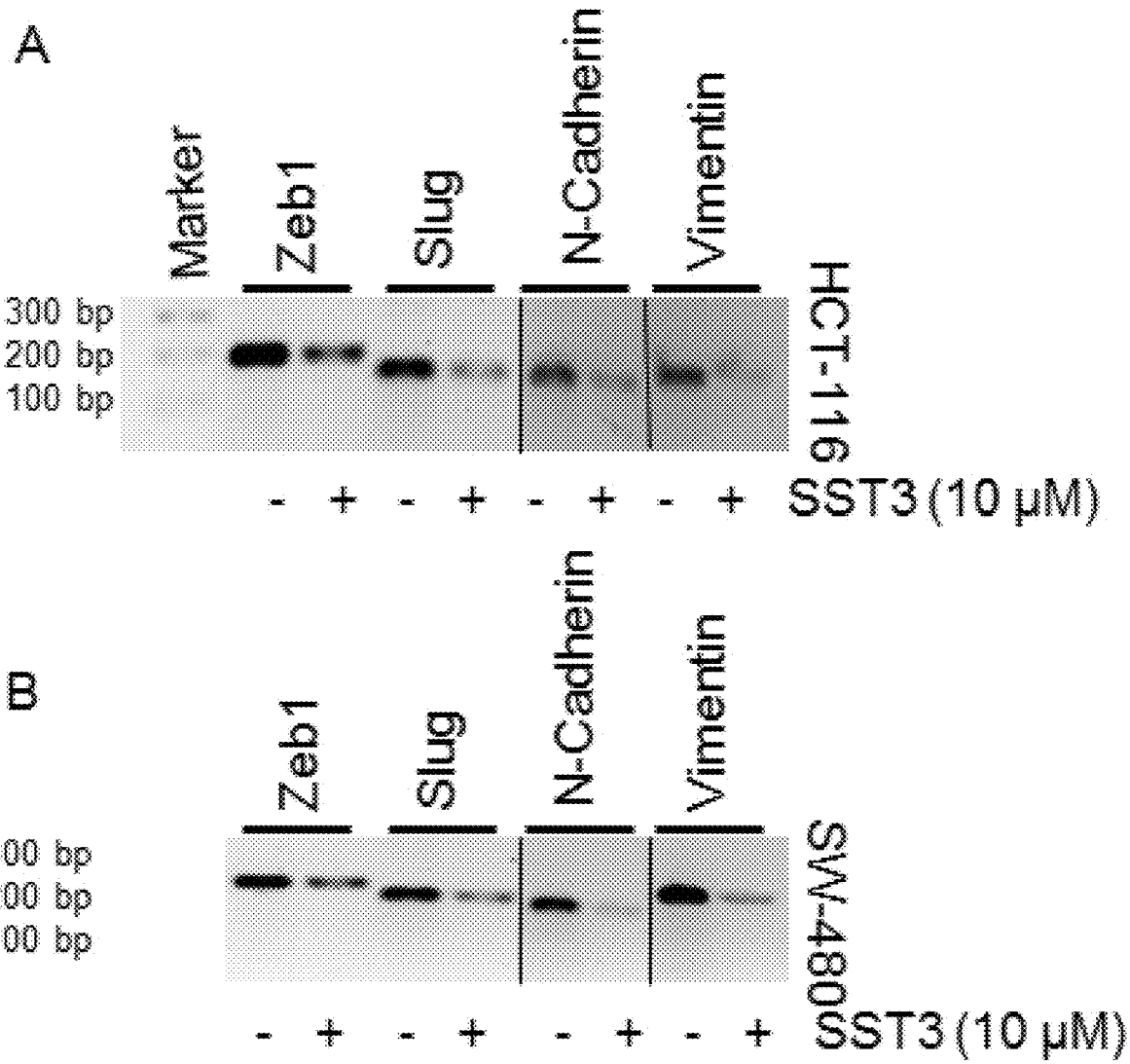
FIG. 7 shows regulation of epithelial-mesenchymal transition (EMT)-related genes by SST3 in colorectal cancer. Colorectal cancer (HCT-116 and SW-480) cells were treated with SST3 (10 μM) for 36 hrs. The expression of Zeb1, Slug, N-Cadherin and vimentin genes was measured by RT-PCR.
Figure 8:
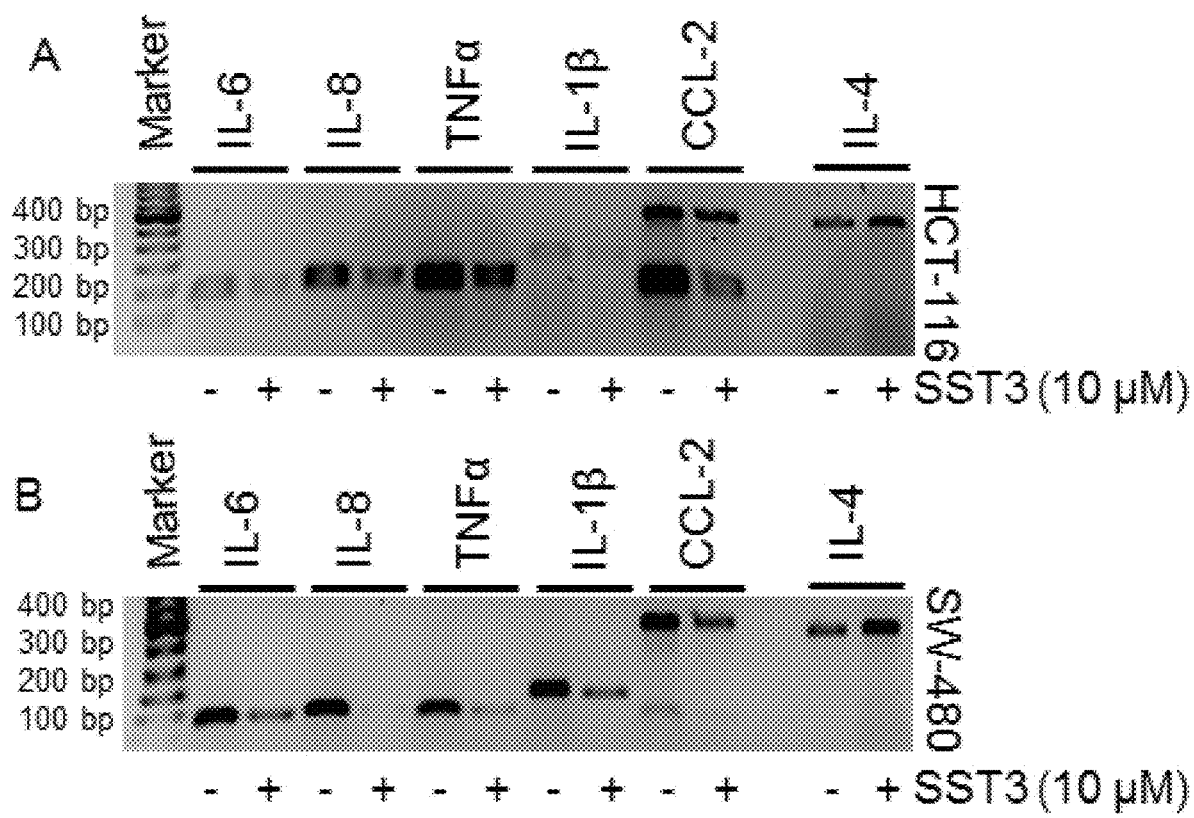
FIG. 8 shows regulation of inflammatory cytokines by SST3 in colorectal cancer. Colorectal cancer HCT-116 and SW-480 cells were treated with SST3 (10 μM) for 36 hrs. The expression of IL-6, IL-8, TNFα, IL-1β, CCL-2, and IL-4 genes was measured by RT-PCR.
Figure 9:
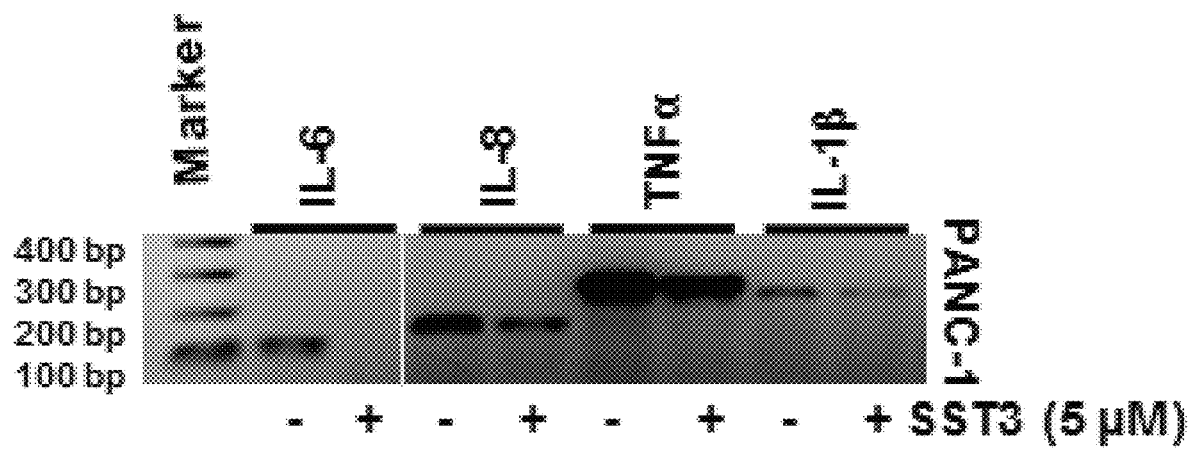
FIG. 9 shows regulation of inflammatory cytokines by SST3 in pancreatic cancer. Pancreatic cancer cells were treated with SST3 (10 μM) for 36 hrs. The expression of IL-6, IL-8, TNFα, and IL-1β genes was measured by RT-PCR.
Figure 10:
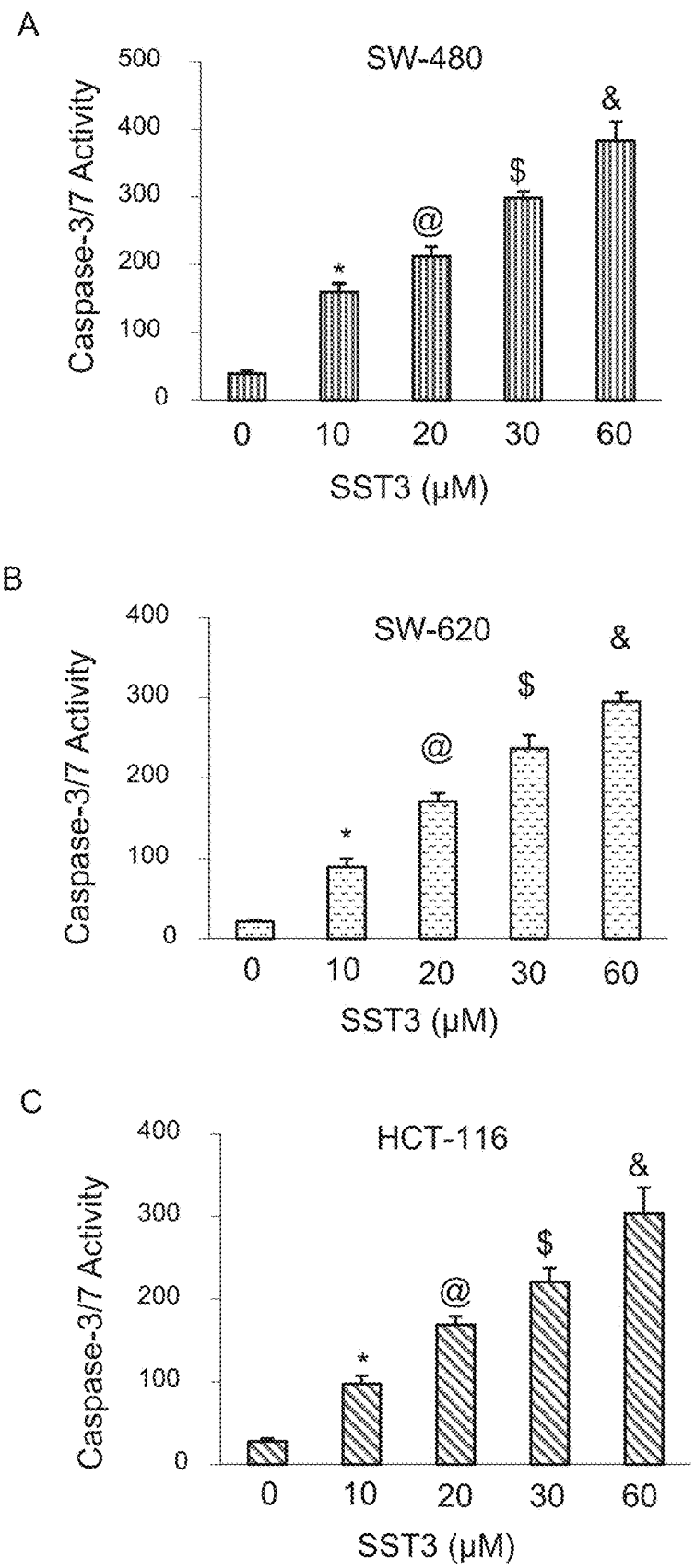
FIG. 10 shows SST3 induces caspase-3/7 activity in colorectal cancer. Colorectal cancer (SW-480, SW-620 and HCT-116) cells were treated with SST3 (10 μM) for 48 hrs. At the end of incubation period, cells were harvested and the caspase-3/7 activity was measured. Data represent mean±SD (n=4). *, @, $ and &=significantly different from control and each other; P<0.05.
Figure 11:
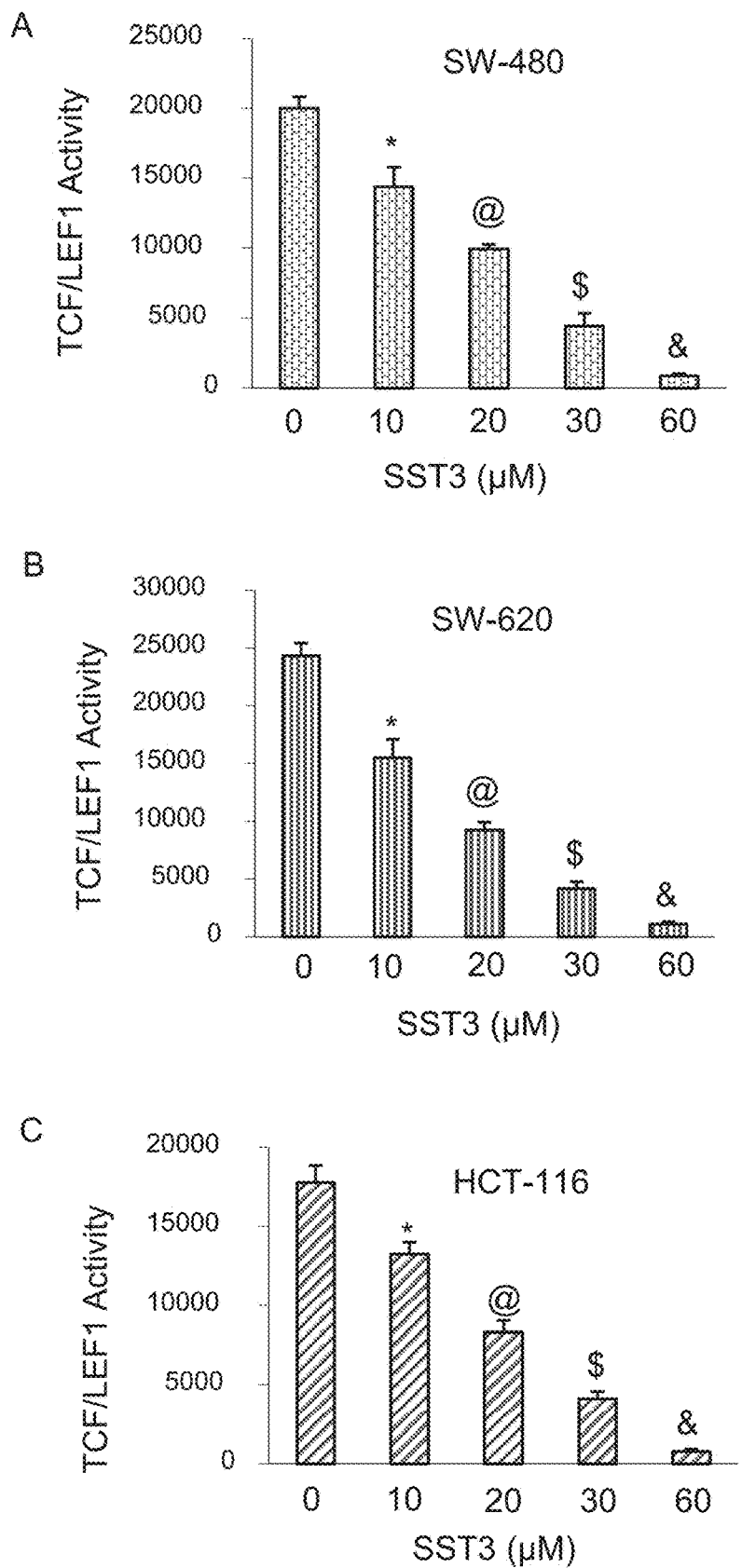
FIG. 11 shows SST3 inhibits TCF/LEF1 transcriptional activity in colorectal cancer. CRC cell lines were stably transduced with TCF/LEF1-responsive GFP/firefly luciferase viral particles (pGreen Fire1-TCF/LEF1 with EF1, System Biosciences). After transduction, cells were treated with SST3 (0-60 μM) for 36 h. TCF/LEF1 reporter activity was measured by luciferase assay as we described. Data represent mean±SD (n=4). *, @, $ and &=significantly different from control and each other; P<0.05.
Figure 12:
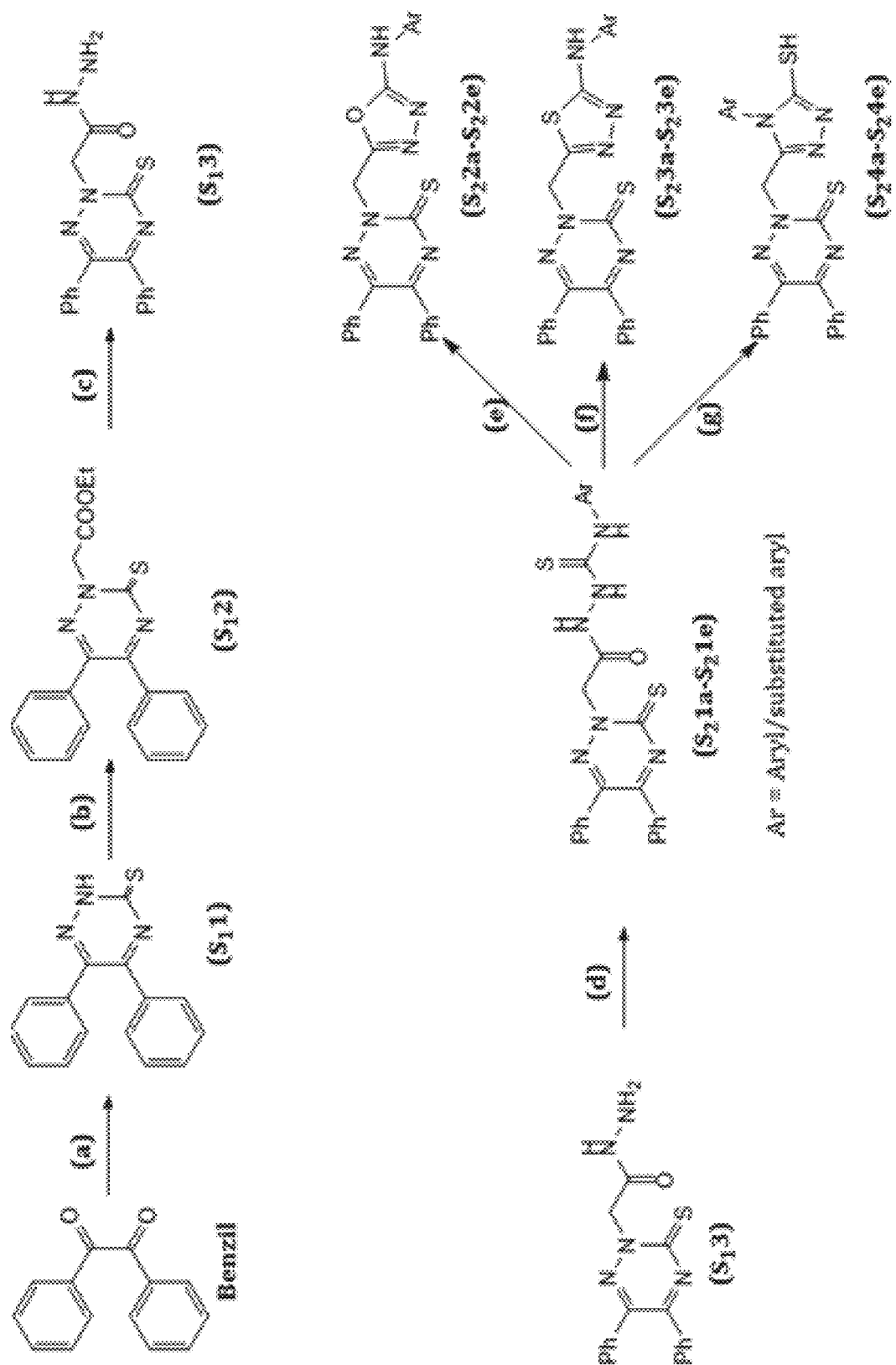
FIG. 12 shows synthesis of some novel $SST_3$ derivatives (i.e., Scheme 1). (a) thiosemicarbazide, Glacial acetic acid, Reflux 6 h (b) $CICH_2COOEt$, N,N-DMF, Reflux 6 h (c) $NH_2NH_2 \cdot H_2O$, ethanol, Reflux 6 h (d) Phenyl/substituted phenyl thioisothiocynate, Ethanol (75% v/v), Reflux 6 h (e) $KI/I_2$, aq. NaOH (5N), Reflux 1 h (f) cold $H_2SO_4$, stirring 4-6 (g) aq. NaOH (4N), Reflux 2 h.
Figure 13:
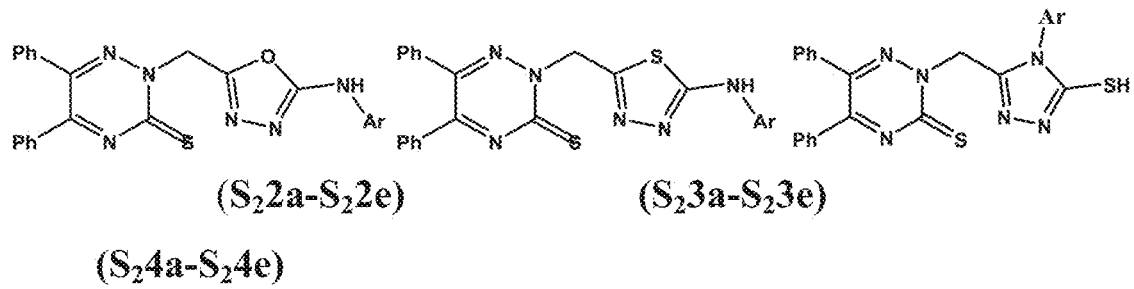
FIG. 13 shows structures of synthesized $SST_3$ derivatives.

Detailed descriptions of one or more embodiments are provided herein. It is to be understood, however, that the present invention can be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Selective COX-2 Inhibitor Compound

Cyclooxygenase (COX) is the key enzyme of arachidonic acid metabolism. Arachidonic acid metabolite, generated by COX, is implicated in cancer pathogenesis, for example the colorectal cancer (CRC) pathogenesis. Multiple lines of evidence indicate that cyclooxygenase-2 (COX-2) is a bonafide pharmacological target for anticancer therapy; however, subsequent development has been limited by unwanted toxic side effects, such as cardiotoxicity and gastric injury. See, for example, Casanova I, Parreño M, Farré L, Guerrero S, Céspedes M V, Pavon M A, Sancho F J, Marcuello E, Trias M, Mangues R Int J Cancer. 2006, 118 (10), 2381-9.

Epidemiological studies show that use of non-steroidal anti-inflammatory drugs (NSAIDs), prototypic inhibitors of COX, is associated with a reduced risk of several malignancies, including colorectal cancer. NSAIDs blockcellular proliferation and induce apoptosis in malignant cells and thereby inhibit tumor growth. Further, several studies have demonstrated that tumor formation and growth are reduced in animals that are either engineered to be COX-2 deficient or treated with a selective COX-2 inhibitor. In clinical trial, treatment with celecoxib, a selective COX-2 inhibitor, reduced the number of colorectal polyps in patients with familial adenomatous polyposis (FAP).

In recent years, several selective COX-2 inhibitors were designed to overcome the problems of toxicity, such as cardiotoxicity and gastric injury (associated with classical NSAIDs). However, most of these drugs were voluntary withdrawn from the market due to cardiovascular toxicity and their effects on gastric injury. Therefore, there is an unmet need to develop effective anti-inflammatory agents with anticancer properties that are non-toxic or with reduced toxicity. Aspects of the invention are directed towards the design, synthesis, characterization and preclinical and clinals uses of novel Prostaglandin Endoperoxide Synthetase-2 (PTGS-2, gene encoding for COX-2) inhibitors or COX-2 inhibitors for the prevention and/or treatment of inflammatory diseases and cancer which are non-toxic or demonstrate reduced toxicity, and which are safe for ulcerogenic, hepatic, and renal funcations and cardiotoxic liabilities.

Aspects of the invention are directed towards compounds that exhibit anti-cancer and/or anti-inflammatory effects which the risk of toxicity is reduced. For example, the compounds can exhibit reduced cardiotoxicity, gastrotoxicity, hepatotoxicity, nephrotoxicity, or any combination thereof.

Aspects of the invention are directed towards a compound of Formula I:

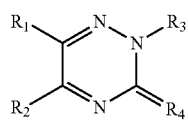
(I)

Wherein,
R$_1$ is an aryl;
R$_2$ is an aryl;
R$_3$ is H; and
R$_4$ is O, or S.
For example, the compound is:

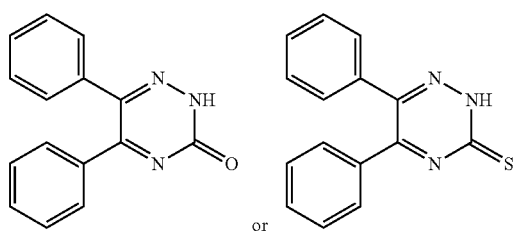

In embodiments, the aryl is phenyl, for example unsubstituted phenyl.

Aspects of the invention are directed towards a compound of Formula II:

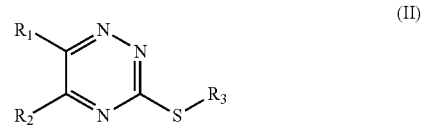
(II)

Where in
R$_1$ is an aryl;
R$_2$ is an aryl; and
R$_3$ is —CH$_2$—CO—OC$_2$H$_5$ or —C$_2$H$_5$.
For example, the compound is:

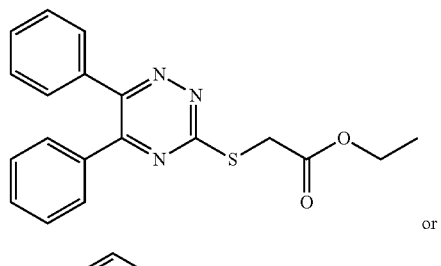

or

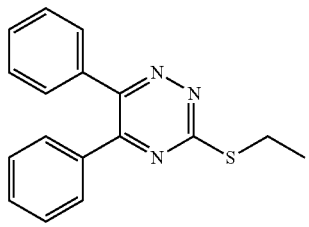

In embodiments, the aryl is phenyl, for example unsubstituted phenyl.

Aspects of the invention are further directed towards a compound of Formula III:

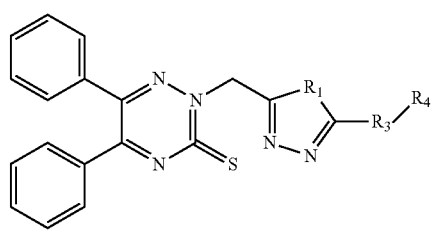
(III)

wherein,
R$_1$ is O, S, or N(R$_2$);
R$_2$ is an aryl group;
R$_3$ is N(R$_5$), or S;
R$_4$ is H; and
R$_5$ is an aryl group.

For example, the compound is

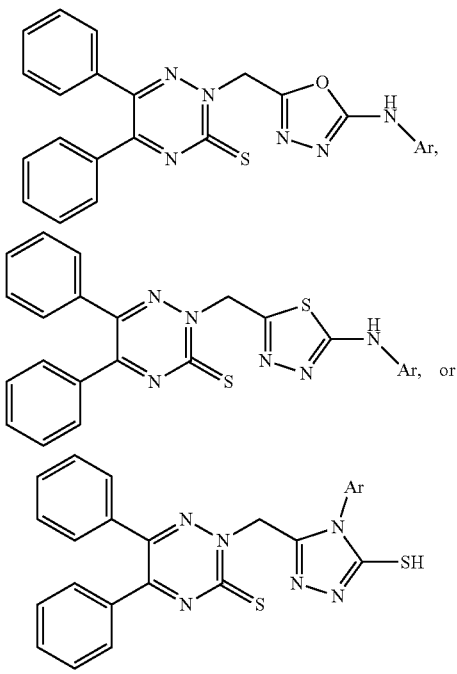

In embodiments, the aryl group (Ar), for example, naphthyl or phenyl non-limiting examples of which comprise 4-Methylphenyl, 4-Methoxyphenyl, 4-Chlorophenyl, or 4-Nitrophenyl.

In embodiments, the compound is a selective COX-2 inhibitor.

Aspects of the invention are further directed towards a pharmaceutical composition comprising a compound described herein and a pharmaceutically acceptable carrier.

In embodiments, the pharmaceutical composition further comprises a second active agent. For example, the second active agent comprises a non-steroidal anti-inflammatory drug (NSAID), a selective COX-2 inhibitor (such as celecoxib, refecoxib, parecoxib and valdecoxib), a non-selective COX inhibitor, or a combination thereof.

Embodiments of the invention demonstrate to have no or reduced levels of toxicity relative to known selective COX-2 inhibitors, such as cardiotoxicity or gastric injury. "Toxicity" can refer to any adverse and/or undesired effect of a compound or pharmaceutical composition on the metabolism or functioning of a cell, tissue, organ or body part, or subject. The amount of toxicity associated with a compound or composition can vary with several conditions including, but not limited to, the amount of compound or composition present, the components present in the composition, the formulation of the composition, the environmental conditions and physiological state of the cell, tissue, organ or body part, or subject, etc. For example, toxicity can refer to cardiotoxicity, gastrotoxicity, hepatotoxicity, or nephrotoxicity.

"Cardiac toxicity," which can also be referred to as "cardiotoxicity," can refer to any toxic side effect on the cardiac system, and can be caused by a medicinal agent administered for the purpose of treating a medical disorder. Cardiac toxicity can be evaluated, for example, based on any one or more of: incidence of symptomatic left ventricular systolic dysfunction (LVSD) or congestive heart failure (CHF), or decrease in left ventricular ejection fraction (LVEF).

"Gastric toxicity," which can also be referred to as "gastrotoxicity," can refer to any toxic side effect on the stomach, and can be caused by a medicinal agent administered for the purpose of treating a medical disorder. Gastrotoxicity can be evaluated, for example, based on any one or more of ulcerogenic liability study. See, for example, I. Szelenyl, K. Thiemer, Distention ulcer as a model for testing of drugs for ulcerogenic side effects, Arch. Toxicol. 41 (1978) 99-105.

The term "hepatotoxicity" can refer to the chemical- or drug-induced liver damage. Drug-induced liver injury or damage is a cause of acute or chronic liver disease. Hepatotoxicity can be caused by certain medicinal agents, when taken in overdoses or sometimes even when introduced within therapeutic ranges. Hepatotoxicity can be evaluated, for example, based on any one or more of liver function tests, such as serum biochemical analysis (A. G. Banerjee, N. Das, S. A. Shengule, R. S. Srivastava and S. K. Shrivastava, Eur J Med Chem. 2015, 101, 81-95) of serum glutamic oxaloacetate transaminase (SGOT), serum glutamic pyruvic transaminase (SGPT), alkaline phosphatase reflecting hepatic functions; or histopathological assessment of liver (A. E. Galigher, E. N. Kozloff, second ed., in: Lea, Febiger (Eds.), Essentials of Practical Microtechnique, vol. 20, Hagerstown Publications, Maryland, USA, 1971, p. 77).

The term "nephrotoxicity" can refer to a condition in which impairment of renal function occurs, and can be caused by a medicinal agent administered for the purpose of treating a medical disorder. Nephrotoxicity can be evaluated, for example, based on any one or more of kidney function tests, such as serum biochemical analysis (e.g., albumin, creatinine and Blood Urea Nitrogen; see for example, A. G. Banerjee, N. Das, S. A. Shengule, R. S. Srivastava and S. K. Shrivastava, Eur J Med Chem. 2015, 101, 81-95); or histopathological assessment of kidney (see, for example, E. Galigher, E. N. Kozloff, second ed., in: Lea, Febiger (Eds.), Essentials of Practical Microtechnique, vol. 20, Hagerstown Publications, Maryland, USA, 1971, p. 77)

In some embodiments, the compound or composition comprising the same has a reduced risk of toxicity, for example when compared to known COX-2 inhibitors such as NSAIDs, when administered to a subject in vivo. For example, the composition can reduce the risk of toxicity by at least about 5%, about 10%, about 15%, about 20%, about 25%, about 30%, about 35%, about 40%, about 45%, or about 50%.

The log P value of a compound is a measure of the compound's hydrophilicity. All the synthesized compounds were evaluated for their experimental log P values using shake-flask method. See, for example, S. O. Podunavac-kuzmanovic, D. D. Cvetkovic, D. J. Barna, The effect of lipophilicity on the antibacterial activity of some 1-benzylbenzimidazole derivatives, J. Serb. Chem. Soc. 73 (2008) 967-978.

Cancer

Aspects of the invention are directed towards compositions and methods for the treatment of cancer. "Cancer" refers to a general term for diseases caused by any type of tumor, such as a malignant tumor. Malignant, as applies to tumors, refers to tumors resulting from abnormal uncontrolled growth of cells and includes, but is not limited to, colorectal cancer, colon cancer, pancreatic cancer, or lung cancer.

Thus, compounds of the invention can be considered "anti-cancer agents" (also referred to as anti-neoplastic agents or anti-tumor agents), which can refer to any agent used in the treatment of cancer or neoplasm. Anti-cancer agents, when used alone or in combination with other compounds, can alleviate, reduce, ameliorate, prevent, or place or maintain in a state of remission of clinical symptoms or diagnostic markers associated with neoplasm, tumor or cancer, and can be used in methods, combinations and compositions provided herein.

Neurological Disorders

Aspects of the invention are directed towards compositions and methods for the treatment of neurological disorders. "Neurological disorder" or "neurological disease" can refer to a general term for diseases of the brain, spine and the nerves that connect them. Non-limiting examples of diseases of the nervous system comprise brain tumors, epilepsy, Parkinson's disease, stroke, and frontotemporal dementia.

Thus, compounds of the invention can be used in the treatment of a neurological disorder, and when used alone or in combination with other compounds, can alleviate, reduce, ameliorate, prevent, or place or maintain in a state of remission of clinical symptoms or diagnostic markers associated with the neurological disorder, and can be used in methods, combinations and compositions provided herein.

Pharmaceutical Combinations

Aspects of the invention are directed towards compositions and methods for the treatment of cancer and inflammatory conditions. Embodiments can comprise selective COX-2 inhibitors as described herein, and can be a component of pharmaceutical combinations for the treatment of cellular proliferative diseases (such as cancer) and/or inflammatory conditions.

The pharmaceutical combinations of the present invention comprise compounds as described herein, such as compounds of Formula I, II and III or IV, in an admixture along with a pharmaceutically acceptable carrier prepared according to conventional pharmaceutical techniques. According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Non-limiting examples of pharmaceutically acceptable carriers comprise solid or liquid fillers, diluents, and encapsulating substances, including but not limited tolactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil. The amount of the carrier employed in conjunction with the combination is sufficient to provide a practical quantity of material per unit dose of the compound.

The use of such media and agents for pharmaceutically active substances is well known in the art. Any conventional media or agent that is compatible with the active compound can be used. Supplementary active compounds can also be incorporated into the compositions.

Pharmaceutically acceptable carriers for oral administration comprise sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Pharmaceutically acceptable carriers for parenteral administration comprise isotonic saline, propylene glycol, ethyl oleate, pyrrolidone, aqueous ethanol, sesame oil, corn oil, and combinations thereof.

Various oral dosages forms can be employed, non-limiting examples of which comprise solid forms such as tablets, capsules, granules, suppositories and/or powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms comprise aqueous solutions, emulsions, suspensions, syrups, aerosols and/or reconstituted solutions and/or suspensions. The composition may alternatively be formulated for external topical application, or in the form of a sterile injectable solution.

Pharmaceutically effective combinations can be provided as a composition comprising between 0.1 and 2000 mg/kg of the compound as described herein, such as compounds of Formula I, II, III, and/or IV. For example, pharmaceutically effective combinations can be provided as a composition comprising about 0.1 mg/kg, 1 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg of a compound as described herein. Useful pharmaceutically effective combinations can contain between about 300 mg/kg and about 1000 mg/kg of the compound as described herein, such as compounds of Formula I, II, III, and/or IV. For example, embodiments as described herein can comprise about 300 mg/kg of a compound.

Pharmaceutically effective combinations, such as a pill or tablet, can be comprise between 0.1 and 2000 mg of an analgesic as described herein, such as compounds of Formula I, II, III, and/or IV. For example, pharmaceutically effective combinations can comprise about 0.1 mg, 1 mg, 10 mg, 20 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1100 mg, 1200 mg, 1300 mg, 1400 mg, 1500 mg, 1600 mg, 1700 mg, 1800 mg, 1900 mg, 2000 mg of a compound as described herein. Useful pharmaceutically effective combinations can contain between about 300 mg and about 1000 mg of a compound as described herein, such as compounds of Formula I, II, III, and/or IV. For example, embodiments as described herein can comprise about 300 mg of a compound as described herein.

The present invention also comprises the formation of pharmaceutically acceptable, stable salts of the compounds as described herein with metals or amines. Non-limiting examples of metals used as cations comprise alkali metals such as $Na^+$ or $K^+$ and alkaline-earth metals such as $Mg^{2+}$ and $Ca^{2+}$. Non-limiting examples of amines comprise N,N-dibenzylethylenediamine, chloro-procaine, choline, diethanolamine, ethylenediamine, N-methylglucamine and procaine.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, nasal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As an exemplary embodiment, pharmaceutical combinations of the invention can be administered orally, either in the form of tablets containing excipients such as starch or lactose, or in capsules, either alone or mixed with excipients, or in the form of syrups or suspensions containing coloring or flavoring agents. They can also be injected parenterally, for example intramuscularly, intravenously or subcutaneously. In parenteral administration, they can be used in the form of a sterile aqueous solution which can contain other solutes, such as, for example, any salt or glucose in order to make the solution isotonic.

The compounds of the present invention can be administered to a subject for the treatment of cancer or an inflammatory condition, for example orally, either covered in gelatin capsules or compressed in lozenges. For oral therapeutic administration, said compounds can be mixed with excipients and used in the form of lozenges, tablets, capsules, elixirs, suspensions, syrups, wafers, chewing gum, and the like. These preparations could contain at least 0.5% of active compound, but can vary depending on each form, in particular between 4% and 75% approximately of the weight of each unit. The amount of active compound in such compositions should be that which is necessary for obtaining the corresponding dosage. For example, the compositions and preparations as described herein can be prepared in such a way that each oral dosage unit can contain between 0.1 mg and 300 mg of the active compound.

In parenteral therapeutic administration, the active compounds of this invention can be incorporated in a solution or suspension. Such preparations, for example, can contain at least 0.1% of the active compound, but can vary between 0.5% and 50% approximately of the weight of the preparation. For example, such preparations comprise about 0.1%, 0.5%, 1%, 5%, 10%, 15%, 25%, 30%, 35%, 40%, 45%, 50%, of the weight of the preparation. The amount of active compound in such compositions should be that which is necessary for obtaining the corresponding dosage. The compositions and preparations as described herein can be prepared in such a way that each parenteral dosage unit can contain between 0.01 mg and 1000 mg, for example between about 0.5 mg and 100 mg of the active compound, for example. While intramuscular administration can be given in a single dose or divided into up to multiple doses, such as three doses, intravenous administration can include a drip device for giving the dose by venoclysis. Parenteral administration can be performed by means of ampoules, disposable syringes or multiple-dose vials made of glass or plastic.

Pharmaceutical compositions suitable for injectable use can include sterile aqueous solutions (where water soluble) or dispersions and sterile powders for the extemporaneous preparation of sterile injectable solutions or dispersions. For intravenous administration, suitable carriers can include physiological saline, bacteriostatic water, Cremophor EM™ (BASF, Parsippany, N.J.) or phosphate buffered saline (PBS). In embodiments, the composition can be sterile and should be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can occur by including an agent in the composition which delays absorption, for example, aluminum monostearate and gelatin.

Sterile injectable solutions can be prepared by incorporating the compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds of the present invention can be administered to a subject in a single dose for the treatment of cancer or an inflammatory condition, or as multiple doses over a period of time. Further, the compound can be administered at intervals of about 4 hours, 8 hours, 12 hours, 24 hours, or longer. In embodiments, the compounds of the invention can be administered continuously over a period of time, such as for 4 hours, 8 hours, 12 hours, 24 hours, or longer.

Of necessity, there will be variations which will depend on the weight and conditions of the subject to be treated and on the particular administration route selected.

Methods of Treatment

Embodiments can be used for the treatment of cancer or an inflammatory condition. "Treatment" can refer to an approach for obtaining beneficial or desired clinical results. For example, the term "treating cancer" or "treatment of cancer" can refer to administration of a compound to a subject afflicted with a cancerous condition alleviates the cancerous condition by killing the cancerous cells, but also to an effect that results in the inhibition of growth and/or metastasis of the cancer. Non-limiting examples of cancers that can be treated by aspects of the invention comprise colorectal cancer, colon cancer, pancreatic cancer, lung cancer, and the like.

Aspects of the invention are directed towards a method of reducing cell viability by contacting a cell, such as a cancer cell, with an effective amount of a compound as described herein.

Aspects of the invention are further directed towards a method of inducing apoptosis of a cell, such as a cancer cell, by contacting a cell with an effective amount of a compound as described herein. In embodiments, apoptosis comprises caspase-dependent apoptosis, such as apoptosis dependent upon caspase 3 and/or caspase 7. In other embodiments, the compound can induce apoptosis by modulating levels of apoptosis-regulatory proteins, such as survivin, Bcl-2, and Bax.

Aspects of the invention are still further directed towards a method of inhibiting cell proliferation of a cell, such as a cancer cell, by contacting a cell with an effective amount of a compound as described herein. Cell proliferation can be indicated, for example, by measuring TCF/LEF1 activity.

Aspects of the invention are also directed towards method of regulating epithelial-mesenchymal transition (EMT) by contacting a cell, such as a cancer cell, with an effective amount of a compound described herein.

Further, aspects of the invention are directed towards a method of inhibiting growth of a cancer cell or tumor by contacting a cell, such as a cancer cell, with an effective amount of a compound described herein. For example, tumor growth can be inhibited by inducing cellular apoptosis and/or inhibiting cellular proliferation.

In embodiments, the compound is a compound of Formula I or II. For example, the compound is:

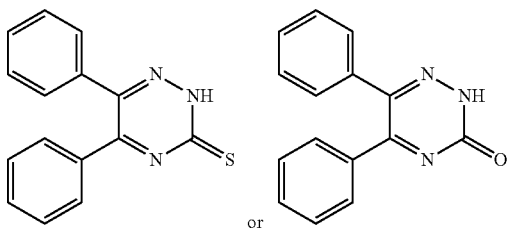

or

In other examples, the compound is:

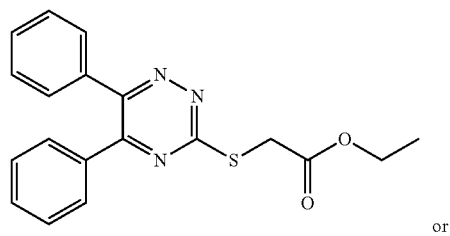

or

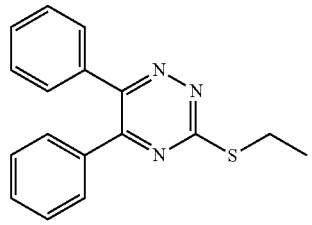

In embodiments, the compound is a compound of Formula IV:

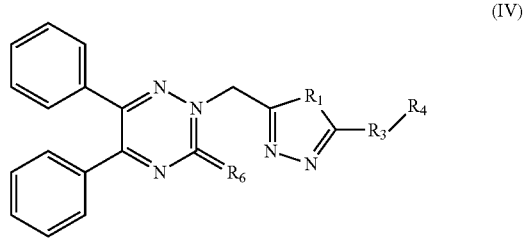

(IV)

wherein, $R_1$ is O, S, or $N(R_2)$;

$R_2$ is an aryl group;

$R_3$ is $N(R_5)$, or S;

$R_4$ is H;

$R_5$ is an aryl group; and $R_6$ is O or S.

For example, the compound is:

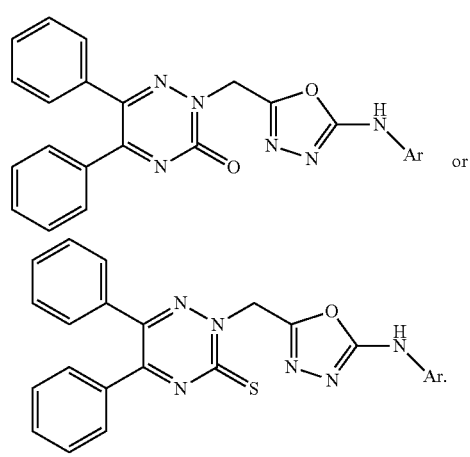

or

In other examples, the compound is:

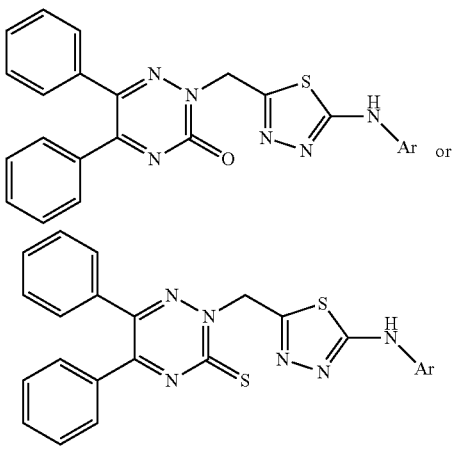 or

In still other examples, the compound is:

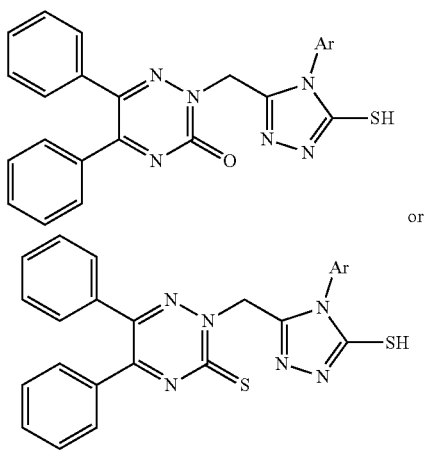

or

As described herein, the aryl group is a napthyl or a phenyl, non-limiting examples of which comprise 4-Methylphenyl, 4-Methoxyphenyl, 4-Chlorophenyl, or 4-Nitrophenyl.

Still further, aspects of the invention are directed towards methods of suppressing an inflammatory response comprising contacting a cell with an effective amount of a compound as described herein.

In embodiments, aspects are directed towards methods of modulating inflammatory cytokines (i.e., cytokines that regulate the inflammatory response) in a cell comprising contacting a cell with an effective amount of a compound as described herein. Non-limiting examples of such inflammatory cytokines comprise pro-inflammatory cytokine (such as IL-6, IL-8, TNFα, IL-1β), anti-inflammatory cytokine (such as IL4), and/or chemokines (such as CCL2).

Aspects of the invention are directed towards methods of administering to a subject compounds that exhibit anti-cancer and/or anti-inflammatory effects while the risk of toxicity is reduced. For example, the compounds can exhibit reduced cardiotoxicity, gastrotoxicity, hepatotoxicity, nephrotoxicity, or any combination thereof. Embodiments can further comprise measuring serum biomarkers to determine toxicity. For example, embodiments can further comprise measuring biomarkers indicative of cardiac function (such as serum cardiac troponin-I (cTnI), serum creatine kinase-MB (CK-MB), or a combination thereof), stomach function, liver function and/or kidney function (such as serum enzymes, total protein, and total albumin), or any combination thereof.

In embodiments, a compound as described herein is used as the only physically active compound in the treatment of cancer without a second active agent.

In other embodiments, the compositions as described herein can be administered to a subject concurrently with and/or in combination with a second active ingredient, such as a non-steroidal anti-inflammatory drug (NSAID), a selective COX-2 inhibitor, a non-selective COX inhibitor, or a combination thereof. Nonsteroidal anti-inflammatory drugs (NSAIDs) block the COX enzymes and reduce prostaglandins throughout the body. As a consequence, ongoing inflammation is reduced. Non-limiting examples of NSAIDs comprise aspirin, celecoxib, diclofenac, diflunisal, etodolac, ibuprofen, indomethacin, ketoprofen, ketorolac, nabumetone, naproxen, oxaprozin, piroxicam, salsalate, sulindac, and tolmetin.

In embodiments, the compound can be administered to a subject prior to contacting a cell. Compounds of as described herein can be incorporated into pharmaceutical compositions suitable for administration to a subject in need thereof. Such compositions can comprise a compound as described herein and a pharmaceutically acceptable carrier. Thus, in some embodiments, the compounds of the invention are present in a pharmaceutical composition.

For example, a pharmaceutical compositions comprising a compound as described herein can be used for treating cancer, such as a therapeutically effective amount of a compound as described herein in admixture with a pharmaceutical acceptable carrier or excipient. For example, a therapeutically effective amount the compound can be administered to a subject in need thereof so as to reduce the size of a tumor, or to prevent the tumor from growing.

Embodiments comprise administering to a subject an effective amount of a composition as described hereinfor the treatment of cancer or inflammatory conditions.

An "effective amount", "sufficient amount" or "therapeutically effective amount" can refer to an amount sufficient to effect beneficial or desired clinical result, such as killing the cancerous cells, inhibiting the growth of the cancer, inhibiting the metastasis of the cancer, and/or reducing or inhibiting inflammation.

Specific compositions as described herein can be administered to a subject by any suitable means, such as oral, intravenous, parenteral, subcutaneous, intrapulmonary, topical, intravitreal, dermal, transmucosal, rectal, and intranasal administration. Parenteral infusions include intramuscular, intravenous, intraarterial, or intraperitoneal administration. The compounds can also be administered transdermally, for example in the form of a slow-release subcutaneous implant or as a transdermal patch. They can also be administered by inhalation. Although direct oral administration may cause some loss of desired activity, the compounds can be packaged in such a way to protect the active ingredient(s) from digestion by use of enteric coatings, capsules or other methods known in the art.

Controlled-release pharmaceutical products have a common goal of improving drug therapy over that achieved by their non-controlled counterparts. The use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Solutions or suspensions used for parenteral, intradermal, or subcutaneous application can include, for example, the following components: a sterile diluent such as water for injection, saline solution, fixed oils, polyethylene glycols, glycerine, propylene glycol or other synthetic solvents; anti-inflammatory agents; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. pH can be adjusted with acids or bases, such as hydrochloric acid or sodium hydroxide.

The dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

A therapeutically effective dose can depend upon a number of factors known to those of ordinary skill in the art. The dose(s) can vary, for example, depending upon the identity, size, and condition of the subject or sample being treated, further depending upon the route by which the composition is to be administered, if applicable, and the effect which the practitioner desires. These amounts can be readily determined by the skilled artisan.

In some embodiments, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 3500 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight.

A therapeutically effective dose can depend upon a number of factors known to those of ordinary skill in the art. The dose(s) can vary, for example, depending upon the identity, size, and condition of the subject or sample being treated, further depending upon the route by which the composition is to be administered, if applicable, and the effect which the practitioner desires. These amounts can be readily determined by the skilled artisan.

A compound as described herein or composition comprising the same can be administered to the subject one time (e.g., as a single injection or deposition). Alternatively, administration can be once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof.

Single unit dosage forms of the disclosure are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal (e.g., cream, lotion, or dermal spray) or transcutaneous administration to a subject. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions or solutions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms for parenteral administration to a subject.

The composition, shape, and type of dosage forms of the disclosure will typically vary depending on their use. Further, the dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

For example, a dosage form used in the acute treatment of a disease can contain larger amounts of one or more of the active agents it comprises than a dosage form used in the chronic treatment of the same disease. Similarly, a parenteral dosage form can contain smaller amounts of one or more of the active agents it comprises than an oral dosage form used to treat the same disease. These and other ways in which specific dosage forms encompassed by this disclosure will vary from one another will be readily apparent to those skilled in the art. See, e.g., Remington's Pharmaceutical Sciences, 18th ed., Mack Publishing, Easton Pa. (1990).

Any of the therapeutic applications described herein can be applied to any subject in need of such therapy, including, for example, a mammal such as a mouse, a rat, a dog, a cat, a cow, a horse, a rabbit, a monkey, a pig, a sheep, a goat, or a human. In some embodiments, the subject is a mouse, rat, pig, or human. In some embodiments, the subject is a mouse.

In some embodiments, the subject is a rat. In some embodiments, the subject is a pig. In some embodiments, the subject is a human.

Medical Kits

Aspects of the invention are directed towards a medical kit suitable for the treatment of cancer or an inflammatory condition comprising printed instructions for administering a compound as described herein to a subject in need thereof; and/or a pharmaceutical composition comprising a compound as described herein and a pharmaceutically acceptable carrier. A "kit" or "medical kit" of the disclosure comprises a dosage form of a compound of the disclosure or a pharmaceutically acceptable salt, solvate, hydrate, stereoisomer, prodrug, or clathrate thereof. A kit can also include two or more compounds as described herein, either in combination, such as in a single tablet, or provided separately, such as in two or more tablets.

Kits can further comprise additional active agents, examples of which are described herein. Kits of the disclosure can further comprise devices that are used to administer the active ingredients. Examples of such devices include, but are not limited to, syringes, drip bags, patches, and inhalers. Kits can also comprise printed instructions for administering the compound to a subject.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Figure 14:
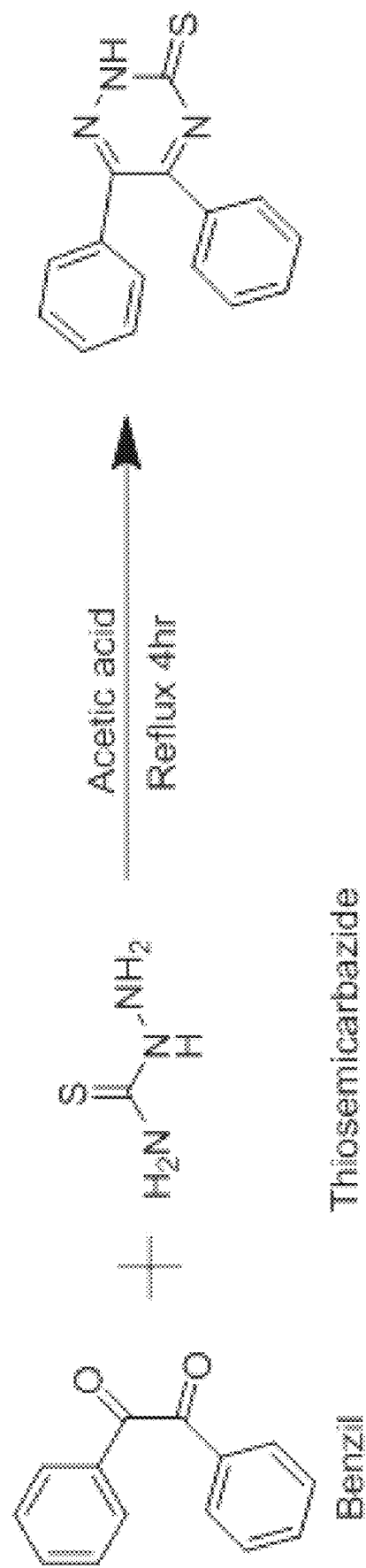
FIG. 14 shows synthesis of 5,6 diphenyl 1,2,4-triazine-3 (2H)-one.
Figure 16:
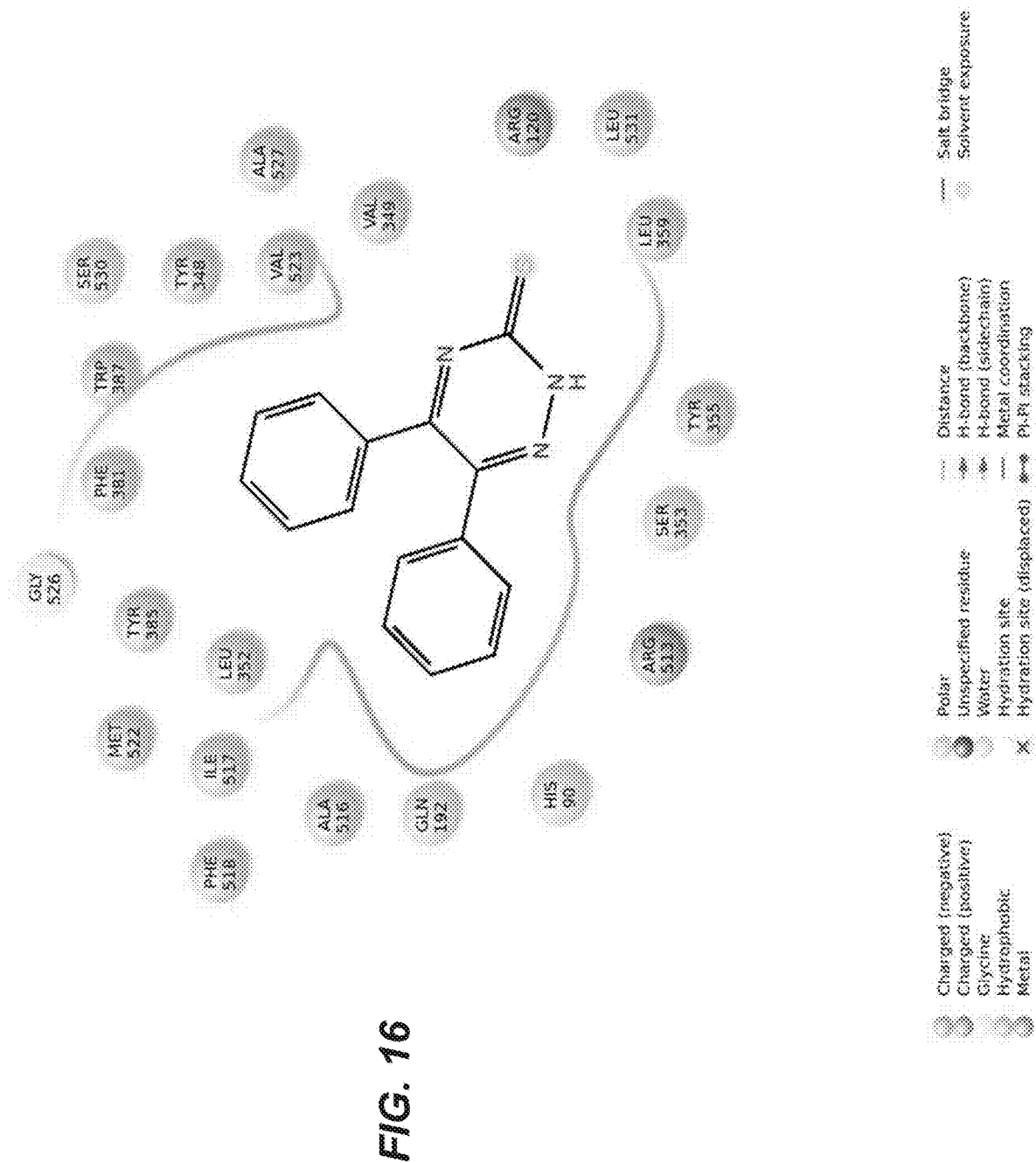
FIG. 16 shows 2D Image of SST13 on COX-1.
Figure 17:
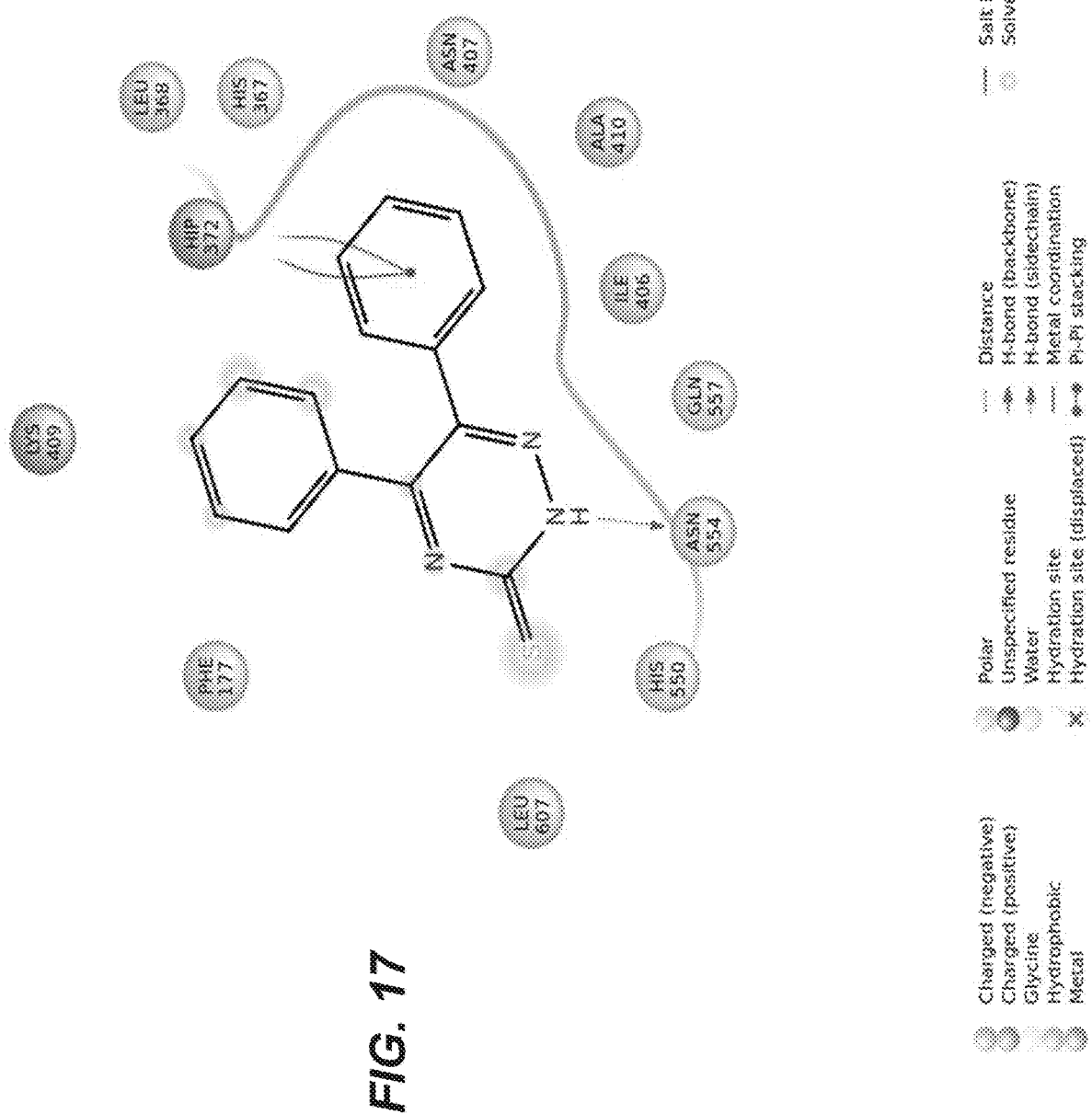
FIG. 17 shows 2D Image of SST13 on 5-LOX.
Figure 18:
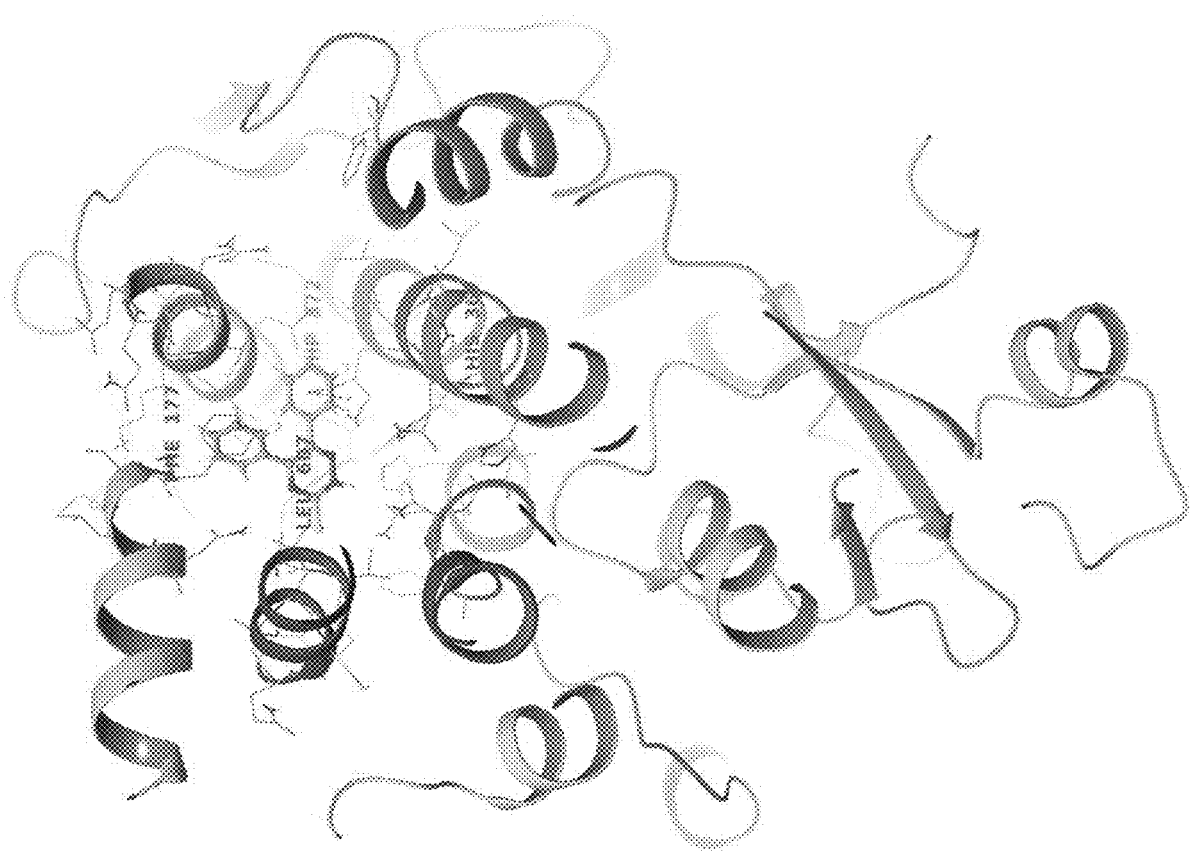
FIG. 18 shows 3D Image of SST13 on 5-LOX.
Figure 19:
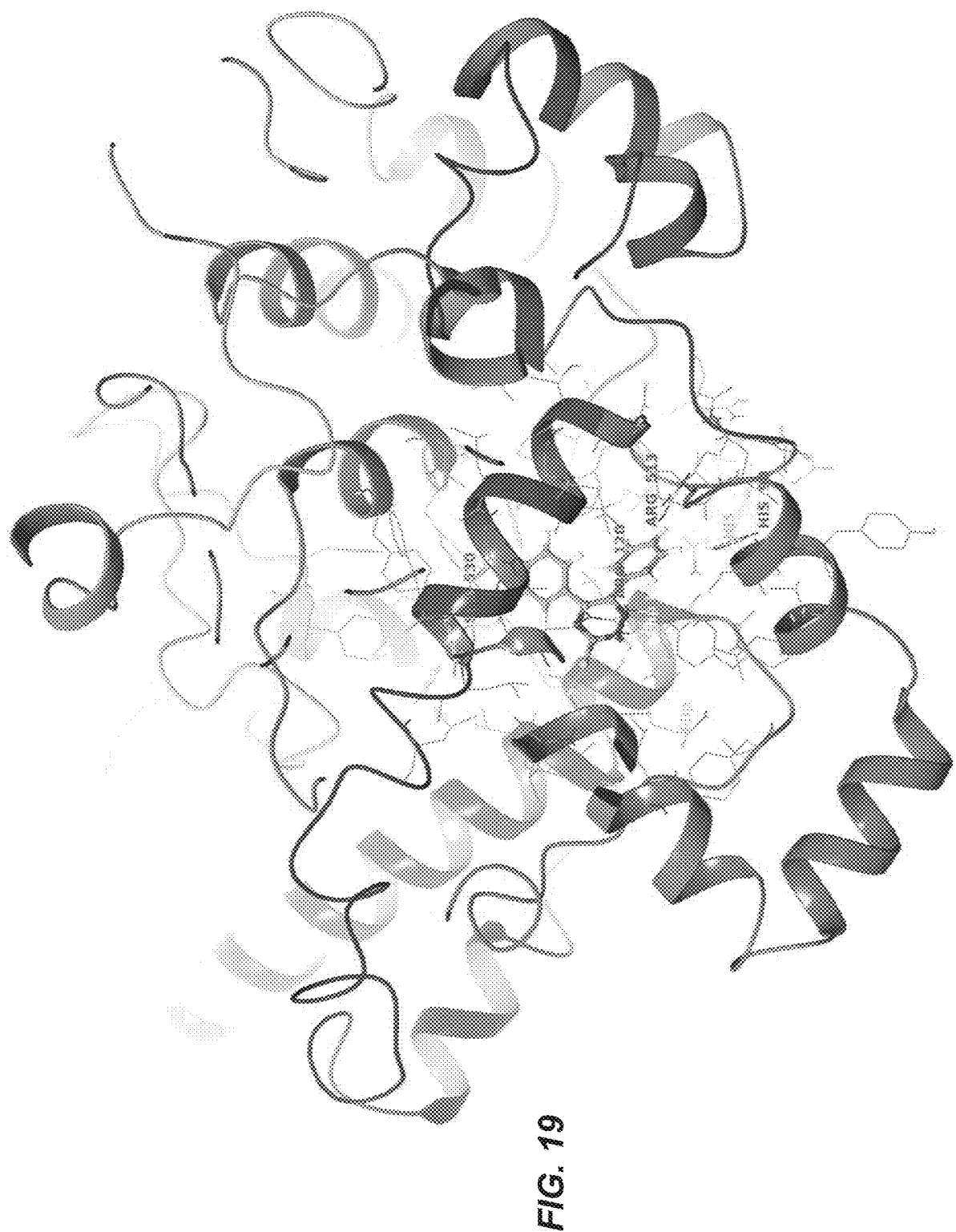
FIG. 19 shows 3D Image of SST13 on COX-1.

Synthesis of 5,6 Diphenyl 1,2,4-Triazine-3(2H)-Thione (See FIG. 14)

Benzil (1 Mol Eq.) was dissolved in glacial acetic acid and added to a solution of thiosemicarbazide (2.2 Mol. Eq.) in hot water. The mixture was refluxed for 4 hr., and the precipitate that appeared was filtered while hot and washed with water until GAA removed. Then it was washed with hexane to remove water. Then yellowish color solid product was obtained. The yellowish crystals obtained were recrystallized from ethanol to give orange crystals.

Yield=90%

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:
1. A compound of Formula IV:

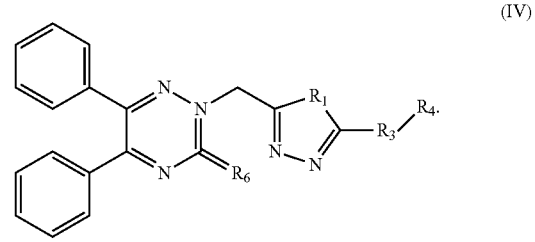

wherein,
$R_1$ is selected from the group consisting of an aryl group, O, S, and $N(R_2)$;
$R_2$ is an aryl;
$R_3$ is selected from the group consisting of H, —$CH_2$—CO—$OC_2H_5$, —$C_2H_5$, $N(R_5)$, and S;
$R_4$ is selected from the group consisting of O, S, and H;
$R_5$ is an aryl group; and
$R_6$ is O.

2. The compound of claim 1, wherein the aryl is selected from a phenyl, a napthyl, or an ethylphenyl.

3. The compound of claim 1, wherein $R_1$ is $N(R_2)$; $R_2$ is an aryl; $R_3$ is S; $R_4$ is H; and $R_6$ is O, and the compound comprises the following chemical structure:

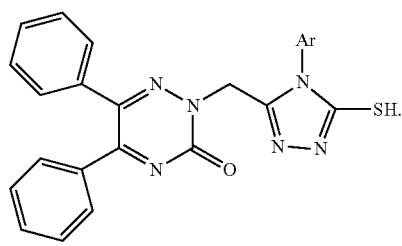

4. The compound of claim 1, wherein $R_1$ is S; $R_3$ is $N(R_5)$; $R_4$ is H; $R_5$ is an aryl group; and $R_6$ is O, and the compound comprises the following chemical structure:

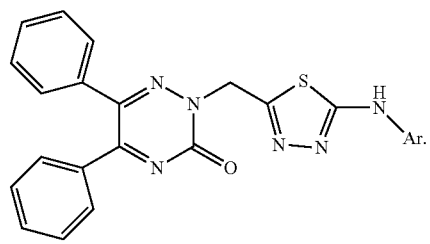

5. The compound of claim 1 wherein $R_1$ is O; $R_3$ is $N(R_5)$; $R_4$ is H; $R_5$ is an aryl group; and $R_6$ is O, and the compound comprises the following chemical structure:

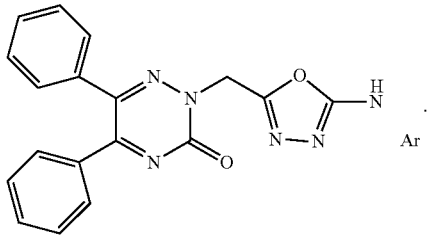

6. A method of reducing cell viability and/or inducing apoptosis of a cell, the method comprising contacting a cell with an effective amount of a compound of Formula IV (IV)

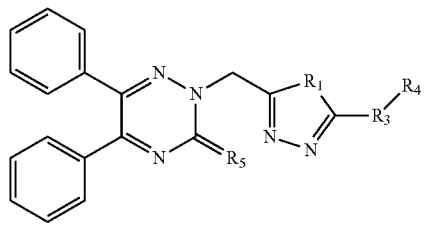

wherein, $R_1$ is selected from the group consisting of an aryl group, O, S, and $N(R_2)$;

$R_2$ is an aryl;

$R_3$ is selected from the group consisting of H, $-CH_2-CO-OC_2H_5$, $-C_2H_5$, $N(R_5)$, and S;

$R_4$ is selected from the group consisting of O, S, and H;

$R_5$ is an aryl group; and $R_6$ is O.

7. The method of claim 6, wherein $R_1$ is O; $R_3$ is $N(R_5)$; $R_4$ is H; $R_5$ is an aryl group; and $R_6$ is O, and the compound comprises the following chemical structure

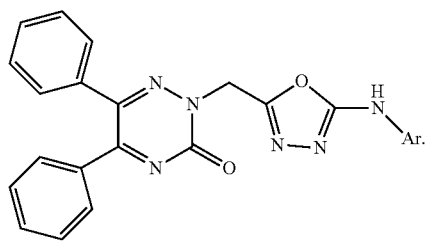

8. The method of claim 6, wherein $R_1$ is S; $R_3$ is $N(R_5)$; $R_4$ is H; $R_5$ is an aryl group; and $R_6$ is O, and the compound comprises the following chemical structure

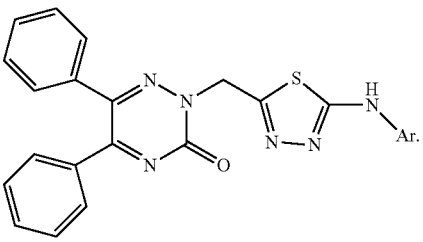

9. The method of claim 6, wherein $R_1$ is $N(R_2)$; $R_2$ is an aryl; $R_3$ is S; $R_4$ is H; and $R_6$ is O, and the compound comprises the following chemical structure:

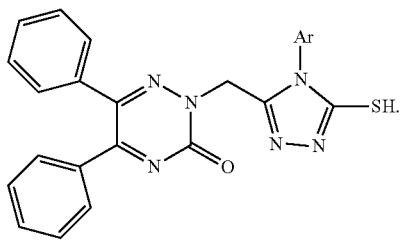

10. A method of inhibiting tumor growth, the method comprising contacting a cell with an effective amount of a compound of Formula IV (IV)

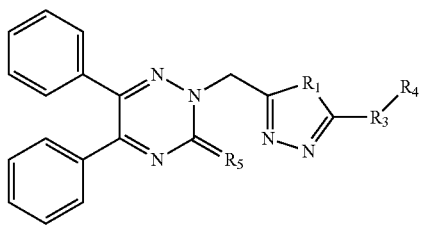

wherein, $R_1$ is selected from the group consisting of an aryl group, O, S, and $N(R_2)$;

$R_2$ is an aryl;

$R_3$ is selected from the group consisting of H, $-CH_2-CO-OC_2H_5$, $-C_2H_5$, $N(R_5)$, and S;

$R_4$ is selected from the group consisting of O, S, and H;

$R_5$ is an aryl group; and $R_6$ is O.

11. The method of claim 10, wherein $R_1$ is O; $R_3$ is $N(R_5)$; $R_4$ is H; $R_5$ is an aryl group; and $R_6$ is O, and the compound comprises the following chemical structure:

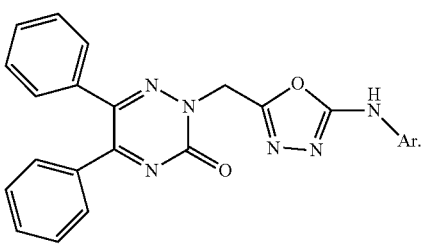

12. The method of claim 10, wherein
R₁ is S; R₃ is N(R₅); R₄ is H; R₅ is an aryl group; and R₆ is O, and the compound comprises the following chemical structure:

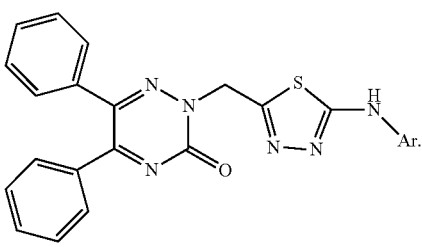

13. The method of claim 10, wherein
R₁ is N(R₂); R₂ is an aryl; R₃ is S; R₄ is H; and R₆ is O, and the compound comprises the following chemical structure:

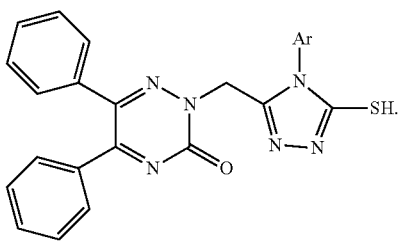

14. A method comprising contacting a cell with an effective amount of a compound of Formula IV

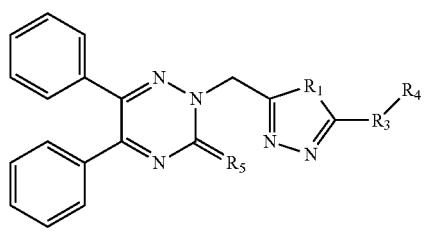

(IV)

wherein,
R₁ is O, S, and N(R₂);
R₂ is an aryl group;
R₃ is N(R₅), or S;
R₄ is H;
R₅ is an aryl group; and
R₆ is O.

15. The method of claim 14, whereby such method is used for reducing cell viability and/or inducing apoptosis.

16. The method of claim 14, whereby such method is used for inhibiting tumor growth.

17. The method of claim 16, wherein the aryl group is phenyl.

18. The method of claim 14, wherein R₁ is S; R₃ is N(R₅); R₄ is H; R₅ is an aryl group; and R₆ is O, and the compound comprises the following chemical structure:

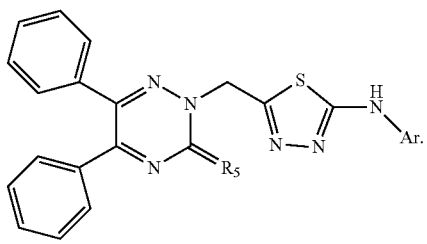

19. The method of any one of claim 14, wherein R₁ is N(R₂); R₂ is an aryl; R₃ is S; R₄ is H; and R₆ is O, and the compound comprises the following chemical structure:

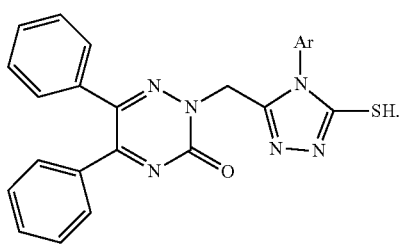

20. The method of claim 14, whereby such method is used for suppressing an inflammatory response.

21. The method of claim 14, whereby such method is used for modulating an inflammatory cytokine in a cell.

22. The method of claim 14, wherein the cell is a cancer cell.

23. The method of claim 22, wherein said cancer is selected from the group consisting of breast cancer, prostate cancer, lung cancer, colon cancer, ovarian cancer, gastric cancer, pancreatic cancer, liver cancer, brain cancer, mesothelioma, melanoma, multiple myeloma, leukemia and lymphoma.

24. The method of claim 14, wherein the compound is administered to a subject.

25. The method of claim 24, wherein the compound is administered in a single dose, continuously, or intermittently.

26. The method of claim 25, wherein the compound is administered orally, parentally, transdermally, or nasally.

27. The method of claim 24, wherein the subject is afflicted with a neurological disorder.

28. A pharmaceutical composition comprising a compound of Formula IV and a pharmaceutically acceptable carrier,

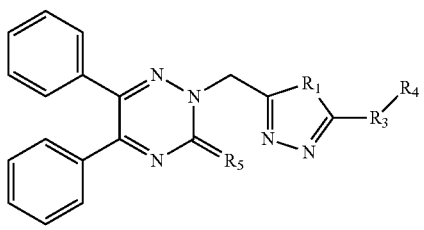

(IV)

wherein $R_1$ is selected from the group consisting of an aryl group, O, S, and $N(R_2)$; $R_2$ is an aryl; $R_3$ is selected from the group consisting of H, —$CH_2$—CO—$OC_2H_5$, —$C_2H_5$, $N(R_5)$ and S; $R_4$ is selected from the group consisting of O, S, and H; $R_5$ is an aryl group; and $R_6$ is O.

29. The pharmaceutical composition of claim 28, wherein the compound is selected from the group consisting of:

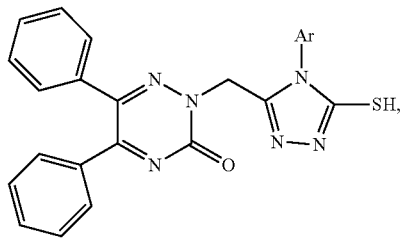

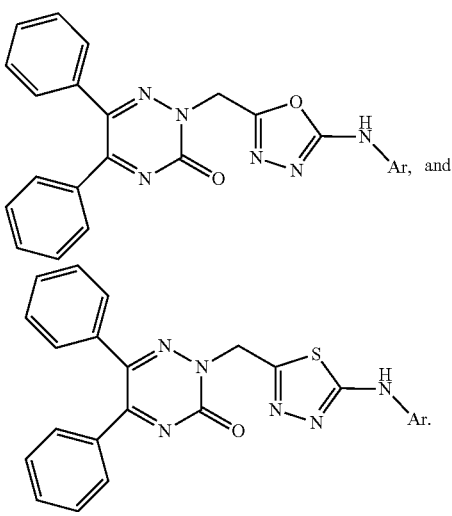

30. The pharmaceutical composition of claim 28, further comprising a second active agent.
31. The pharmaceutical composition of claim 30, wherein the second active agent comprises a non-steroidal anti-inflammatory drug (NSAID), a selective COX-2 inhibitor, a non-selective COX inhibitor, or a combination thereof.
32. A medical kit suitable for the treatment of cancer, comprising:
printed instructions for administering a compound to a subject afflicted with a cancer, and a pharmaceutical composition including said compound and a pharmaceutically acceptable carrier, wherein said compound comprises the following chemical structure:

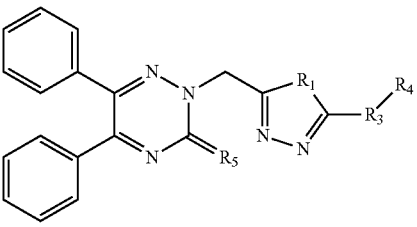

wherein R1 is selected from the group consisting of an aryl group, O, S, and $N(R_2)$; $R_2$ is an aryl; $R_3$ is selected from the group consisting of H, —$CH_2$—CO—$OC_2H_5$, —$C_2H_5$, $N(R_5)$, and S; $R_4$ is selected from the group consisting of O, S, and H; $R_5$ is an aryl group; and $R_6$ is O.

33. The method of claim 6, wherein the aryl group is a phenyl, a napthyl, or an ethylphenyl.
34. The method of claim 6, wherein the cell is a cancer cell.
35. The method of claim 6, wherein the compound is administered to a subject in a single dose, continuously, or intermittently.
36. The method of claim 35, wherein the subject is afflicted with a neurological disorder.
37. The method of claim 10, wherein the aryl group is a phenyl, a napthyl, or an ethylphenyl.
38. The method of claim 10, wherein the cell is a cancer cell.
39. The method of claim 10, wherein the compound is administered to a subject in a single dose, continuously, or intermittently.
40. The method of claim 39, wherein the subject is afflicted with a neurological disorder.
41. The method of claim 10, further comprising inhibiting cell proliferation.
42. The method of claim 17, wherein the phenyl comprises 4-methylphenyl, 4-methoxyphenyl, 4-chlorophenyl, or 4 nitrophenyl.
43. The method of claim 14, wherein $R_1$ O; $R_3$ is $N(R_5)$; $R_4$ is H; $R_5$ is an aryl group; and $R_6$ is O, and the compound comprises the following chemical structure

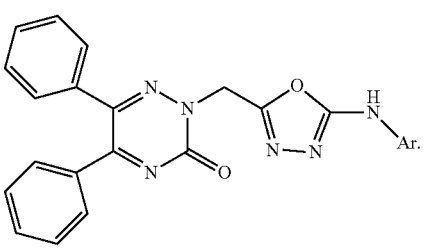

44. The method of claim 14, wherein the aryl group is a napthyl.
45. The method of claim 16, further comprising inhibiting cell proliferation.

* * * * *